US010436752B2

(12) United States Patent
Inoue et al.

(10) Patent No.: US 10,436,752 B2
(45) Date of Patent: Oct. 8, 2019

(54) PARTICULATE MEASUREMENT APPARATUS AND PARTICULATE MEASUREMENT SYSTEM

(71) Applicant: NGK Spark Plug Co., LTD., Nagoya (JP)

(72) Inventors: Yoshinori Inoue, Nagoya (JP); Yuichi Goto, Konan (JP); Ryosuke Noda, Kakamigahara (JP)

(73) Assignee: NGK Spark Plug Co., LTD., Nagoya (JP)

( * ) Notice: Subject to any disclaimer, the term of this patent is extended or adjusted under 35 U.S.C. 154(b) by 191 days.

(21) Appl. No.: 15/714,258

(22) Filed: Sep. 25, 2017

(65) Prior Publication Data

US 2018/0088082 A1    Mar. 29, 2018

(30) Foreign Application Priority Data

Sep. 28, 2016    (JP) .................................. 2016-189891

(51) Int. Cl.
| | |
|---|---|
| *G01N 27/68* | (2006.01) |
| *F01N 11/00* | (2006.01) |
| *F02D 41/14* | (2006.01) |
| *F02D 41/22* | (2006.01) |
| *G01N 15/06* | (2006.01) |

(Continued)

(52) U.S. Cl.
CPC ............. *G01N 27/68* (2013.01); *F01N 11/00* (2013.01); *F02D 41/1466* (2013.01); *F02D 41/222* (2013.01); *G01N 15/0656* (2013.01); *F01N 2560/05* (2013.01); *F02P 9/007* (2013.01); *G01N 2015/0046* (2013.01); *Y02T 10/40* (2013.01); *Y02T 10/47* (2013.01)

(58) Field of Classification Search
CPC ............... G01N 27/68; G01N 15/0656; G01N 2015/0046; F01N 11/00; F01N 2560/05; F02D 41/1466; F02D 41/222; Y02T 10/40; Y02T 10/47; F02P 9/007
USPC .......... 73/23.33, 23.31, 28.02; 250/310, 397, 250/374; 96/26; 324/71.1, 71.4, 324/454–456, 464–465
See application file for complete search history.

(56) References Cited

U.S. PATENT DOCUMENTS

| | | | | |
|---|---|---|---|---|
| 4,531,486 A | * | 7/1985 | Reif .................... | G01N 15/0656 123/198 D |
| 7,406,855 B2 | * | 8/2008 | Tikkanen ............... | G01N 27/62 73/23.31 |

(Continued)

FOREIGN PATENT DOCUMENTS

| | | | |
|---|---|---|---|
| JP | 2005024409 A | * | 1/2005 |
| JP | 2013-195069 A | | 9/2013 |

(Continued)

*Primary Examiner* — Jermele M Hollington
*Assistant Examiner* — Sean Curtis
(74) *Attorney, Agent, or Firm* — Leason Ellis LLP

(57) ABSTRACT

A particulate measurement apparatus comprises a control section, which provisionally determines in an anomaly determination process that a corona core wire is in a short anomaly state when a linear voltage is equal to or lower than a particular voltage value and increments a sensor anomaly counter CNS or a chassis anomaly counter. The control section determines that the corona core wire is in a short anomaly state when the count value of one of the anomaly counters is equal to or greater than a determination threshold.

8 Claims, 6 Drawing Sheets

(51) Int. Cl.
    *G01N 15/00*   (2006.01)
    *F02P 9/00*    (2006.01)

(56) References Cited

U.S. PATENT DOCUMENTS

| | | | | |
|---|---|---|---|---|
| 9,053,912 B2* | 6/2015 | Kokubo | ................ | H01J 49/022 |
| 9,581,069 B2* | 2/2017 | Motomura | ......... | G01N 15/0656 |
| 9,606,038 B2* | 3/2017 | Okuda | ................... | G01N 27/62 |
| 9,719,907 B2* | 8/2017 | Motomura | ......... | G01N 15/0656 |
| 9,897,528 B2* | 2/2018 | Motomura | ......... | G01N 15/0656 |
| 10,048,223 B2* | 8/2018 | Hisada | .................. | G01N 27/70 |
| 10,094,756 B2* | 10/2018 | Matsuoka | .......... | G01N 15/0606 |
| 10,094,757 B2* | 10/2018 | Hisada | ................. | F01N 11/007 |
| 10,101,257 B2* | 10/2018 | Yazawa | .............. | G01N 15/0656 |
| 2012/0234172 A1* | 9/2012 | Sugiyama | ........... | G01N 1/2252 96/26 |
| 2012/0262182 A1* | 10/2012 | Matsuoka | .......... | G01N 15/0656 324/464 |
| 2013/0219990 A1* | 8/2013 | Allmendinger | .... | G01N 33/0027 73/23.31 |
| 2014/0239185 A1* | 8/2014 | de Oliveira | .......... | G01T 1/2935 250/374 |
| 2014/0326873 A1* | 11/2014 | Kokubo | ................ | H01J 49/022 250/288 |
| 2014/0352405 A1* | 12/2014 | Motomura | ......... | G01N 15/0656 73/23.31 |
| 2015/0020574 A1* | 1/2015 | Motomura | ......... | G01N 15/0656 73/23.31 |
| 2015/0102822 A1* | 4/2015 | Okuda | .................. | G01N 27/62 324/464 |
| 2015/0114087 A1* | 4/2015 | Sugiyama | ........... | G01M 15/102 73/28.01 |
| 2015/0120229 A1* | 4/2015 | Sugiyama | ......... | G01N 15/0606 702/85 |
| 2016/0011093 A1* | 1/2016 | Matsuoka | .......... | G01N 15/0656 73/23.33 |
| 2016/0139098 A1* | 5/2016 | Inoue | ................. | G01N 33/0054 702/189 |
| 2017/0160234 A1* | 6/2017 | Suzuki | ................ | G01M 15/102 |
| 2017/0343463 A1* | 11/2017 | Minami | .............. | F02D 41/1466 |
| 2018/0088018 A1* | 3/2018 | Inoue | ................. | G01N 15/0656 |
| 2018/0088082 A1* | 3/2018 | Inoue | ..................... | G01N 27/68 |
| 2018/0143107 A1* | 5/2018 | Murase | ................ | G01M 15/102 |
| 2018/0164203 A1* | 6/2018 | Koerber | ................... | B03C 3/06 |
| 2019/0064112 A1* | 2/2019 | Osawa | ................. | G01N 27/626 |
| 2019/0085748 A1* | 3/2019 | Sugiyama | ............... | F01N 11/00 |

FOREIGN PATENT DOCUMENTS

| | | | | |
|---|---|---|---|---|
| JP | 2015036647 A | * | 2/2015 | |
| JP | 2018054428 A | * | 4/2018 | ............. G01N 27/68 |
| JP | 2018054475 A | * | 4/2018 | ......... G01N 15/0656 |

* cited by examiner

PARTICULATE MEASUREMENT APPARATUS AND PARTICULATE MEASUREMENT SYSTEM

This application claims the benefit of Japanese Patent Application No. 2016-189891, filed Sep. 28, 2016, which is incorporated herein by reference in its entirety.

FIELD OF THE INVENTION

The present invention relates to a particulate measurement apparatus and a particulate measurement system which measure the amount of particulates such as soot contained in a gas under measurement.

BACKGROUND OF THE INVENTION

Conventionally, there has been known a particulate measurement system which measures the amount of particulates (e.g., soot) contained in a gas under measurement, or target gas (for example, exhaust gas discharged from an internal combustion engine or the like) (see, for example, Japanese Patent Application Laid-Open (kokai) No. 2013-195069).

Such a particulate measurement system includes a particulate sensor which is exposed to the gas under measurement and detects particulates, and a particulate measurement apparatus which is electrically connected to the particulate sensor through a corona cable and controls the particulate sensor.

The particulate sensor includes an ion generation section, an electrification chamber, and a trapping section. The particulate measurement apparatus includes an isolation transformer for corona discharge, a particulate computation section, and a corona discharge control section. The corona cable includes a corona core wire for electrically connecting the ion generation section and the isolation transformer for corona discharge, and a shield wire for covering the corona core wire in a state in which the shield wire is electrically insulated from the corona core wire.

Through use of ions generated at the ion generation section by means of corona discharge, the particulate measurement system electrifies at least a portion of particulates contained in the gas under measurement in the electrification chamber to produce electrified particulates. The particulate measurement system measures the amount of particulates on the basis of a current which flows in accordance with the amount of the electrified particulates discharged from the particulate sensor to the outside.

Problem to be Solved by the Invention

However, such a particulate measurement system has the following problem. Due to the influence of application of external force or the manner of handling of the particulate sensor by a user, an anomaly of the electrical connection state (for example, a short anomaly in which a short circuit is formed between the corona core wire and the shield wire) may occur at the corona cable, the ion generation section, etc., and an expensive apparatus is required to determine such an anomalous state.

Namely, since high voltage is applied to the corona cable and the ion generation section, direct detection of the voltages from the corona cable and the ion generation section requires an expensive detection apparatus which can withstand high voltage. Use of such an expensive detection apparatus causes the problem of increased production cost of the particulate measurement apparatus and the particulate measurement system.

An object of the present invention is to provide a particulate measurement apparatus and a particulate measurement system which can determine an anomaly of the electrical connection state at the corona cable, the ion generation section, etc. without requiring the direct detection of voltage at the corona cable or the ion generation section.

SUMMARY OF THE INVENTION

Means for Solving the Problem

A particulate measurement apparatus according to one aspect of the present inventions is adapted to be electrically connected to a particulate sensor for detecting particulates contained in a target gas and controls the particulate sensor so as to measure the amount of the particulates contained in the target gas. The particulate measurement apparatus comprises an isolation transformer for corona discharge, a signal line, a particulate computation section, a corona discharge control section, and an anomaly determination section.

The particulate sensor includes an ion generation section, an electrification chamber, an ion trapping section, and a metallic support.

The ion generation section generates ions by means of corona discharge. The electrification chamber is a chamber into which the target gas is introduced and which electrifies, by using the ions, the particulates contained in the target gas to thereby produce electrified particulates. The trapping section traps the ions generated by the ion generation section but not used for the electrification of the particulates. The metal support supports the ion generation section, the electrification chamber, and the trapping section in a condition in which the metal support is electrically insulated from the ion generation section, the electrification chamber, and the trapping section.

The isolation transformer for corona discharge has a primary coil and a secondary coil and performs voltage conversion. The signal line forms at least a portion of a signal path extending from the trapping section to a line of a secondary-side reference potential which is a reference potential of the secondary coil. The particulate computation section computes the amount of the particulates contained in the target gas on the basis of the current value of compensation current supplied to the signal line in accordance with the amount of the electrified particulates discharged from the particulate sensor. The corona discharge control section controls the amount of electric power supplied to the primary coil, on the basis of secondary-side current flowing through the signal path, so as to control ion electric power generated at the secondary coil. Notably, the ion electric power is electric power for generating ions at the ion generation section.

The particulate measurement apparatus is electrically connected to the particulate sensor through a corona cable. The corona cable includes a corona core wire, an inner shield wire, and an outer shield wire.

The corona core wire forms at least a portion of a path for supplying electric power from the secondary coil to the ion generation section. The inner shield wire is electrically connected to the trapping section and the signal line in a state in which the inner shield wire is electrically insulated from the corona core wire. The outer shield wire is electrically connected to the metal support and a line of a primary-side reference potential which is a reference potential of the primary coil in a state in which the outer shield wire is electrically insulated from the corona core wire and the inner shield wire.

The anomaly determination section determines whether or not the corona core wire is in a short anomaly state on the basis of a state of control of the amount of electric power supplied to the primary coil by the corona discharge control section, the short anomaly state being an anomalous state in which the corona core wire is electrically connected to the inner shield wire or the outer shield wire.

In such a particulate measurement apparatus, when an anomaly of the electrical connection state (for example, an anomaly of short between the corona core wire and the inner shield wire, an anomaly of short between the corona core wire and the outer shield wire, etc.) has occurred at the corona cable, the ion generation section, etc., the supply of electric power from the secondary coil to the ion generation section is not performed properly. In this case, since the ion generation section cannot generate ions properly, the generation of electrified particulates at the electrification chamber cannot be performed properly, and the trapping of ions at the trapping section cannot be performed properly. Therefore, the current flowing from the trapping section to the signal line through the inner shield wire exhibits an anomalous behavior different from that in the case where the electrical connection state is normal. The secondary-side current also exhibits an anomalous behavior different from that in the case where the electrical connection state is normal.

Notably, the corona discharge control section controls the amount of electric power supplied to the primary coil on the basis of the secondary-side current. Therefore, in the case where the secondary-side current exhibits an anomalous behavior, the state of control of the amount of electric power supplied to the primary coil by the corona discharge control section becomes a special state different from that in the case where the secondary-side current is normal.

Therefore, the anomaly determination section can determine the anomaly of the electrical connection state at the corona cable, the ion generation section, etc. (the short anomaly state of the corona core wire or the like) on the basis of the state of control of the amount of electric power supplied to the primary coil by the corona discharge control section. Examples of the short anomaly state of the corona core wire include a short anomaly state in which a short circuit is formed between the corona core wire and the inner shield wire and a short anomaly state in which a short circuit is formed between the corona core wire and the outer shield wire.

As a result, the particulate measurement apparatus can determine the anomaly of the electrical connection state at the corona cable, the ion generation section, etc. without directly detecting the voltage at the corona cable or the ion generation section.

Notably, the current value of the compensation current supplied to the signal line in accordance with the amount of electrified particulates discharged from the particulate sensor to the outside shows a value corresponding to the amount of the electrified particulates and shows a value corresponding to the amount of the particulates contained in the target gas. Also, the current value of the compensation current is not limited to a numerical value which directly represents the current value of the compensation current and may be a numerical value which indirectly represents the current value of the compensation current. For example, the current value of the compensation current may be a numerical value represented through use of any of other state quantities which correlate with the current value of the compensation current, for example, a voltage value which correlates with the current value of the compensation current.

In the above-described particulate measurement apparatus, the anomaly determination section may determine that the corona core wire is in the short anomaly state when the state of control of the amount of electric power supplied to the primary coil by the corona discharge control section is a voltage drop anomalous control state in which the voltage applied to the primary coil falls within a predetermined voltage drop anomaly range.

If the short anomaly state is a short anomaly state in which the corona core wire is electrically connected to the inner shield wire, the current produced by the ion electric power generated at the secondary coil flows to the line of the secondary-side reference potential through the corona core wire, the inner shield wire, and the signal line. In this case, since all the current produced by the ion electric power flows through the signal line, the secondary-side current flowing through the signal line assumes the maximum value.

Also, if the short anomaly state is a short anomaly state in which the corona core wire is electrically connected to the outer shield wire, the current produced by the ion electric power generated at the secondary coil flows to the line of the primary-side reference potential through the corona core wire and the outer shield wire. In this case, the current produced by the ion electric power does not flow through the signal line. However, since the compensation current is supplied from the particulate computation section to the signal line, the secondary-side current flowing through the signal line assumes the maximum value.

In the case where the secondary-side current assumes the maximum value, the corona discharge control section determines that the ion electric power generated at the secondary coil has reached a control target value and performs a power minimization control for controlling the amount of electric power supplied to the primary coil to become equal to or smaller than the minimum value of a proper power range determined in advance. For example, in the case of a configuration in which the corona discharge control section controls the amount of electric power supplied to the primary coil by controlling the voltage applied to the primary coil, the corona discharge control section performs, as the power minimization control, a process of controlling the amount of electric power supplied to the primary coil such that the voltage applied to the primary coil becomes equal to or lower than the minimum value of a proper voltage range determined in advance.

Namely, in the case of the short anomaly state in which the corona core wire is electrically connected to the inner shield wire or the outer shield wire, the corona discharge control section controls the amount of electric power supplied to the primary coil such that the voltage applied to the primary coil becomes equal to or lower than the minimum value of the proper voltage range.

"A voltage range equal to or lower than the minimum value of the proper voltage range" is defined as a voltage drop anomaly range. In this case, in the short anomaly state in which the corona core wire is electrically connected to the inner shield wire or the outer shield wire, the corona discharge control section controls the amount of electric power supplied to the primary coil such that the control state enters a voltage drop anomaly control state in which the voltage applied to the primary coil falls within the voltage drop anomaly range.

Therefore, it is possible to determine whether or not the corona core wire is in the short anomaly state by determining whether or not the state of control of the amount of electric power supplied to the primary coil by the corona discharge control section is in the voltage drop anomaly control state (the control state in which the voltage applied to the primary coil falls within the voltage drop anomaly range determined in advance).

In the above-described particulate measurement apparatus, the anomaly determination section may determine that the corona core wire is in the short anomaly state when the voltage drop anomalous control state created by the corona discharge control section continues for a predetermined short anomaly time or longer.

Namely, in the case where the state of the control by the corona discharge control section enters the voltage drop anomaly control state, the anomaly determination section does not immediately determine that the corona core wire is in the short anomaly state. Instead, the anomaly determination section determines whether or not the corona core wire is in the short anomaly state on the basis of the result of the determination as to whether or not the voltage drop anomaly control state continues for the short anomaly time or longer. By performing the anomaly determination in the above-described manner, the anomaly determination section is prevented from erroneously determining that the corona core wire is in the short anomaly state when the state of the control by the corona discharge control section temporarily enters the voltage drop anomaly control state due to the influence of noise or the like.

Therefore, the particulate measurement apparatus can decrease the frequency of occurrence of erroneous determination due to the influence of noise or like and thus can improve the determination accuracy in determining the short anomaly state.

In the above-described particulate measurement apparatus, the anomaly determination section may determine whether the short anomaly state is a primary-side short anomaly or a secondary-side short anomaly on the basis of the current value of the compensation current in addition to the state of control of the amount of electric power supplied to the primary coil by the corona discharge control section, the primary-side short anomaly being an anomalous state in which the corona core wire is electrically connected to the outer shield wire, the secondary-side short anomaly being an anomalous state in which the corona core wire is electrically connected to the inner shield wire.

In this particulate measurement apparatus, as described above, when an anomaly of the electrical connection state at the corona cable, the ion generation section, etc. has occurred, the supply of electric power from the secondary coil to the ion generation section is not performed properly, and the ion generation section cannot generate ions properly. As a result, the generation of electrified particulates at the electrification chamber cannot be performed properly, and the trapping of ions at the trapping section cannot be performed properly. Therefore, the current value of the compensation current which is supplied to the signal line in accordance with the amount of electrified particulates discharged from the particulate sensor to the outside exhibits an anomalous behavior different from that in the case where the electrical connection state is normal.

Therefore, the anomaly determination section can determine the anomaly of the electrical connection state at the corona cable, the ion generation section, etc. (the short anomaly state of the corona core wire, etc.) by performing the determination on the basis of the current value of the compensation current in addition to the state of control of the amount of electric power supplied to the primary coil by the corona discharge control section.

As described above, through use of a plurality of determination factors, including the current value of the compensation current and the state of control of the amount of electric power supplied to the primary coil by the corona discharge control section, it is possible to improve the determination accuracy, as compared with the case where the determination is made through use of a single determination factor.

In the above-described particulate measurement apparatus, the anomaly determination section may determine that the short anomaly state is the primary-side short anomaly, in which the corona core wire is electrically connected to the outer shield wire, in the case where the current value of the compensation current falls within a predetermined current increase anomaly range and the state of control of the amount of electric power supplied to the primary coil by the corona discharge control section is a voltage drop anomalous control state in which a voltage applied to the primary coil falls within a predetermined voltage drop anomaly range, and the anomaly determination section may determine that the short anomaly state is the secondary-side short anomaly, in which the corona core wire is electrically connected to the inner shield wire, in the case where the current value of the compensation current does not fall within the current increase anomaly range and the state of control of the amount of electric power supplied to the primary coil by the corona discharge control section is the voltage drop anomalous control state.

In the case of a primary-side short anomaly state in which the corona core wire is electrically connected to the outer shield wire, the current produced by the ion electric power generated at the secondary coil flows to the line of the primary-side potential through the corona core wire and the outer shield wire. In this case, there is created a state which is the same as the state in which substantially all the ions are discharged to the outside of the particulate sensor. Therefore, the compensation current supplied to the signal line assumes a large value. Namely, the current value of the compensation current supplied to the signal line falls within a region of the numerical range of the current value of the compensation current, the region being not near the smallest value but being near the largest value. A range which is a portion of the numerical range of the current value of the compensation current and which is equal to or larger than a predetermined value is defined as a current increase anomaly range. As can be understood from above, the anomaly determination section can determine that the short anomaly state is the primary-side short anomaly when the state of control of the amount of electric power to the primary coil by the corona discharge control section is in the voltage drop anomaly control state and the current value of the compensation current falls within the current increase anomaly range.

Also, in the case of the secondary-side short anomaly in which the corona core wire is electrically connected to the inner shield wire, the current produced by the ion electric power generated at the secondary coil flows to the line of the secondary-side potential through the corona core wire, the inner shield wire, and the signal line. In this case, since all the current produced by the ion electric power flows through the signal line, substantially no compensation current is supplied to the signal line, and the current value of the compensation current become small. Namely, the current value of the compensation current supplied to the signal line falls within a region of a numerical range of the current value of the compensation current, the region being not near the largest value but being near the smallest value. As can be understood from above, the anomaly determination section can determine that the short anomaly state is the secondary-side short anomaly when the state of control of the amount of electric power to the primary coil by the corona discharge control section is in the voltage drop anomaly control state and the current value of the compensation current falls outside the current increase anomaly range.

Namely, in the case where the state of control of the amount of electric power to the primary coil by the corona discharge control section is determined to be in the voltage drop anomaly control state, a determination as to whether or not the current value of the compensation current falls within the current increase anomaly range is further made so as to determine whether the short anomaly state of the corona core wire is the primary-side short anomaly state or the secondary-side short anomaly state.

As a result, according to the particulate measurement apparatus, it is possible to determine whether the short anomaly state of the corona core wire is the primary-side short anomaly state or the secondary-side short anomaly state by performing the determination on the basis of the current value of the compensation current in addition to the state of control of the amount of electric power to the primary coil by the corona discharge control section.

Notably, for the determination as to whether or not the short anomaly is the secondary-side short anomaly, instead of the "determination as to whether or not the current value of the compensation current falls within the current increase anomaly range," the "determination as to whether or not the current value of the compensation current falls within a current drop anomaly range" may be employed. Notably, a range which is a portion of the numerical range of the current value of the compensation current, which is equal to or smaller than a predetermined value, and which does not overlap the current increase anomaly range is defined as the current drop anomaly range.

In the above-described particulate measurement apparatus, the anomaly determination section may determine that the short anomaly state is the primary-side short anomaly, in which the corona core wire is electrically connected to the line of the primary-side reference potential, in the case where a state in which the state of control of the amount of electric power supplied to the primary coil by the corona discharge control section is the voltage drop anomalous control state and the current value of the compensation current falls within the current increase anomaly range continues for a predetermined primary short anomaly time or longer, and the anomaly determination section may determine that the short anomaly state is the secondary-side short anomaly, in which the corona core wire is electrically connected to the line of the secondary-side reference potential, in the case where a state in which the state of control of the amount of electric power supplied to the primary coil by the corona discharge control section is the voltage drop anomalous control state and the current value of the compensation current does not fall within the current increase anomaly range continues for a predetermined secondary short anomaly time or longer.

Namely, in the case where the state of the control by the corona discharge control section enters the voltage drop anomaly control state and the current value of the compensation current falls within the current increase anomaly range, the anomaly determination section does not immediately determine that the corona core wire is in the primary-side short anomaly state. Instead, the anomaly determination section determines whether or not the corona core wire is in the primary-side short anomaly state on the basis of the result of a determination as to whether or not such a state continues for the primary short anomaly time or longer.

Also, in the case where the state of the control by the corona discharge control section enters the voltage drop anomaly control state and the current value of the compensation current falls outside the current increase anomaly range, the anomaly determination section does not immediately determine that the corona core wire is in the secondary-side short anomaly state. Instead, the anomaly determination section determines whether or not the corona core wire is in the secondary-side short anomaly state on the basis of the result of a determination as to whether or not such a state continues for the secondary short anomaly time or longer.

By performing the anomaly determination in the above-described manner, the anomaly determination section is prevented from erroneously determining that the corona core wire is in the short anomaly state (the primary-side short anomaly state, the secondary-side short anomaly state) in the case where a state in which "the state of the control by the corona discharge control section is in the voltage drop anomaly control state and the current value of the compensation current falls within or falls outside the current increase anomaly range" temporarily occurs due to the influence of noise or the like.

Therefore, the particulate measurement apparatus can decrease the frequency of occurrence of erroneous determination due to the influence of noise or like and thus can improve the determination accuracy in determining the short anomaly state of the corona core wire.

The above-described particulate measurement apparatus may further comprise an informing section which informs that the corona core wire is in the short anomaly state in the case where the anomaly determination section determines that the corona core wire is in the short anomaly state.

Since the informing section is provided so as to inform the short anomaly state of the corona core wire, it is possible to prompt a user of the particulate measurement apparatus to check the connection state of the corona cable or to exchange the corona cable.

As a result, the particulate measurement apparatus can prevent the particulate measurement using the particulate sensor from being continued in a situation in which the corona core wire is in the short anomaly state, to thereby prevent lowering of the measurement performance of the particulate sensor.

A particulate measurement system of another aspect of the present invention comprises a particulate sensor for detecting particulates contained in a target gas; and a particulate measurement apparatus which is electrically connected to the particulate sensor through a corona cable and which controls the particulate sensor so as to measure the amount of the particulates contained in the target gas, wherein the particulate measurement apparatus is the above-described particulate measurement apparatus.

The particulate measurement system, which is configured by connecting the particulate sensor to the above-described particulate measurement apparatus through the corona cable, can determine the anomaly of the electrical connection state at the corona cable, the ion generation section, etc. without directly detecting the voltage at the corona cable or the ion generation section.

Effect of the Invention

The particulate measurement apparatus and the particulate measurement system of the present invention can determine the anomaly of the electrical connection state at the corona cable, the ion generation section, etc. without directly detecting the voltage at the corona cable or the ion generation section.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 1A and 1B are explanatory views used for describing the overall configuration of a particulate measurement system, wherein FIG. 1A is an explanatory view exemplifying a general configuration of a vehicle on which the particulate measurement system is mounted, and FIG. 1B is an explanatory view exemplifying a general configuration of the particulate measurement system attached to the vehicle.

DETAILED DESCRIPTION OF THE INVENTION

Embodiments to which the present invention is applied will next be described with reference to the drawings.

The present invention is not limited to the following embodiments, but can be embodied in various modes so long as the modes fall within the technical scope of the present invention.

1. First Embodiment

[1-1. Overall Configuration]

The configuration of a particulate measurement system according to the present embodiment will be described.

Figure 1A:
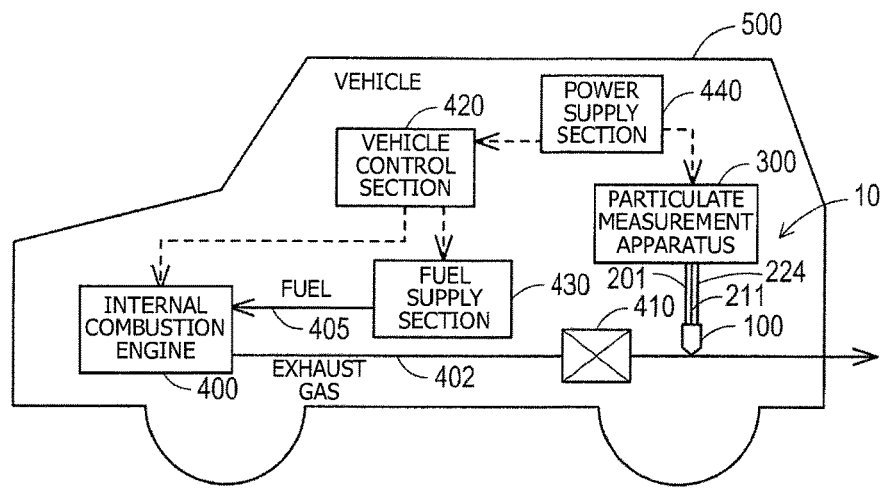
Figure 1B:
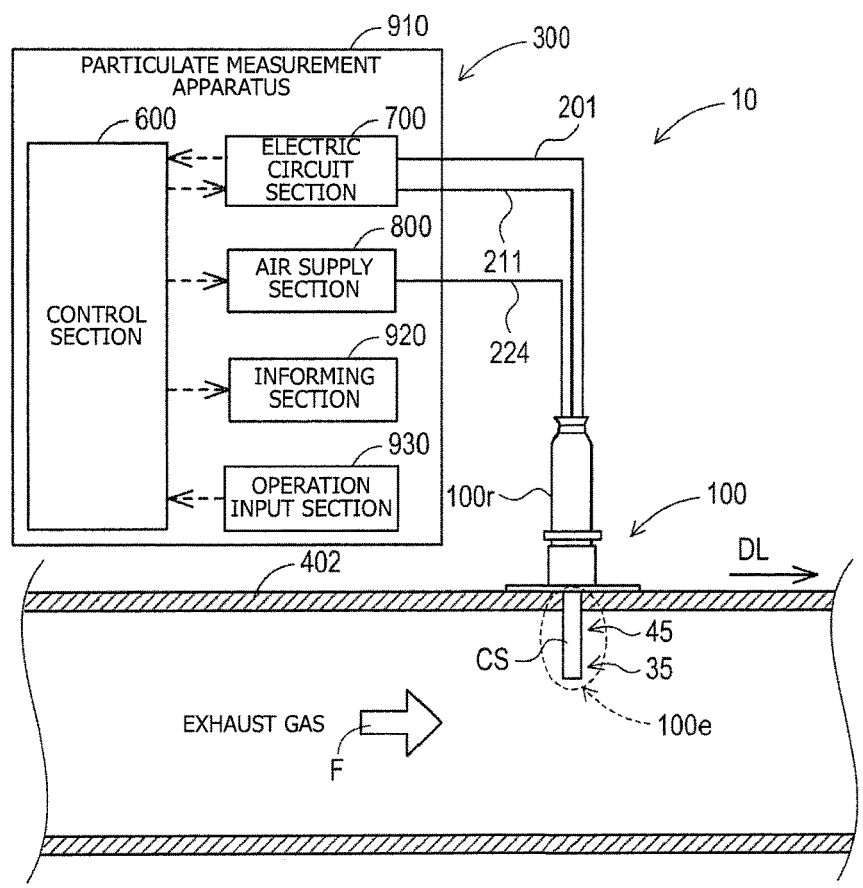

FIGS. 1A and 1B are explanatory views used for describing the overall configuration of a particulate measurement system 10 according to the first embodiment. FIG. 1A is an explanatory view schematically exemplifying the general configuration of a vehicle 500 on which the particulate measurement system 10 is mounted. FIG. 1B is an explanatory view exemplifying the general configuration of the particulate measurement system 10 attached to the vehicle 500.

The particulate measurement system 10 includes a particulate sensor 100, a corona cable 201, an auxiliary cable 211, an air supply tube 224, and a particulate measurement apparatus 300, and measures the amount of particulates such as soot contained in exhaust gas discharged from an internal combustion engine 400. The internal combustion engine 400, which is a power source of the vehicle 500, is a diesel engine or the like.

The particulate sensor 100 is attached to an exhaust pipe 402 extending from the internal combustion engine 400, and is electrically connected to the particulate measurement apparatus 300 through the corona cable 201 and the auxiliary cable 211. In the present embodiment, the particulate sensor 100 is attached to a portion of the exhaust pipe 402, which portion is located downstream of a filter apparatus 410 (for example, a DPF (diesel particulate filter)). The particulate sensor 100 outputs to the particulate measurement apparatus 300 a signal which correlates with the amount of particulates contained in the exhaust gas.

The particulate measurement apparatus 300 drives the particulate sensor 100 and detects (measures) the amount of particulates contained in the exhaust gas on the basis of the signal input from the particulate sensor 100. The "amount of particulates contained in the exhaust gas" detected by the particulate measurement apparatus 300 may be a value which is proportional to the sum of the surface areas of particulates contained in the exhaust gas or a value which is proportional to the sum of the masses of the particulates. Alternatively, the amount of particulates contained in the exhaust gas may be a value which is proportional to the number of particulates contained in a unit volume of the exhaust gas. The amount of particulates contained in the exhaust gas, which is detected by the particulate measurement apparatus 300, can be used for, for example, analysis of the operation state (combustion state, etc.) of the internal combustion engine 400 and determination of the state of the filter apparatus 410 (deterioration determination, anomaly determination, etc.).

In accordance with signals sent from various portion of the vehicle 500, the vehicle control section 420 controls the combustion state of the internal combustion engine 400, the amount of fuel supplied from a fuel supply section 430 to the internal combustion engine 400 through a fuel pipe 405, etc. The particulate measurement apparatus 300 and the vehicle control section 420 are electrically connected to a power supply section 440, and electric power is supplied from the power supply section 440 to the particulate measurement apparatus 300 and the vehicle control section 420.

As shown in FIG. 1B, the particulate sensor 100 has a cylindrical distal end portion 100e, and is fixed to the outer surface of the exhaust pipe 402 such that the distal end portion 100e is inserted into the exhaust pipe 402. In the present embodiment, the distal end portion 100e of the particulate sensor 100 is inserted approximately perpendicular to an extension direction DL of the exhaust pipe 402. A casing CS of the distal end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing through the exhaust pipe 402 is introduced into the interior of the casing CS of the distal end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described later.

Notably, in the present embodiment, of end portions of the particulate sensor 100 in the longitudinal direction, the end portion where the inflow hole 45 is provided will be referred to as the "distal end portion (side)," and the end portion opposite the forward end portion will be referred to as the "proximal or rear end portion (side)."

The corona cable 201, the auxiliary cable 211, and the air supply tube 224 are attached to a rear end portion 100r of the particulate sensor 100. Each of the corona cable 201, the auxiliary cable 211, and the air supply tube 224 is formed of a flexible member. The corona cable 201 and the auxiliary cable 211 are electrically connected to an electric circuit section 700 of the particulate measurement apparatus 300, and the air supply tube 224 is connected to an air supply section 800 of the particulate measurement apparatus 300.

The particulate measurement apparatus 300 includes a control section 600, the electric circuit section 700, and the air supply section 800, a housing 910, an informing section 920, and an operation input section 930.

The housing 910 has a box-like shape and accommodates the control section 600, the electric circuit section 700, the air supply section 800, the informing section 920, and the operation input section 930. Notably, the housing 910 is configured to allow a user to carry the housing 910. Thus, the user can carry the particulate measurement apparatus 300 to a vehicle to which the particulate sensor 100 is to be attached, and can mount the particulate measurement apparatus 300 onto the vehicle for use.

The informing section 920 includes a display unit disposed on the housing 910 and displays various pieces of information (images, character strings, numerical expressions, etc.) on the display screen of the display unit on the basis of instructions from the control section 600.

The operation input section 930 includes switches, a touch panel, a voice input device, etc. disposed on the housing 910, and outputs to the control section 600 input operation information for determining an input operation performed by the user through use of the switches, the touch panel, the voice input device, etc.

The control section 600, which includes a microcomputer, executes various types of processes on the basis of input information from the electric circuit section 700 and the operation input section 930, and controls the electric circuit section 700, the air supply section 800, and the informing section 920. Also, the control section 600 detects (measures) the amount of particulates contained in the exhaust gas from a signal supplied from the electric circuit section 700.

The electric circuit section 700 supplies electric power for driving the particulate sensor 100 through the corona cable 201 and the auxiliary cable 211. A signal which correlates with the amount of particulates contained in the exhaust gas is input from the particulate sensor 100 to the electric circuit section 700 through at least one of the corona cable 201 and the auxiliary cable 211. Using this signal input from the particulate sensor 100, the electric circuit section 700 outputs to the control section 600 a signal corresponding to the amount of particulates contained in the exhaust gas. These signals will be described in detail later.

The air supply section 800 includes a pump (not shown), and supplies high-pressure air to the particulate sensor 100 through the air supply tube 224 on the basis of an instruction from the control section 600. The high-pressure air supplied from the air supply section 800 is used for drive of the particulate sensor 100. Notably, the type of the gas supplied by the air supply section 800 may be other than air.

[1-2. Particulate Sensor]

Figure 2:
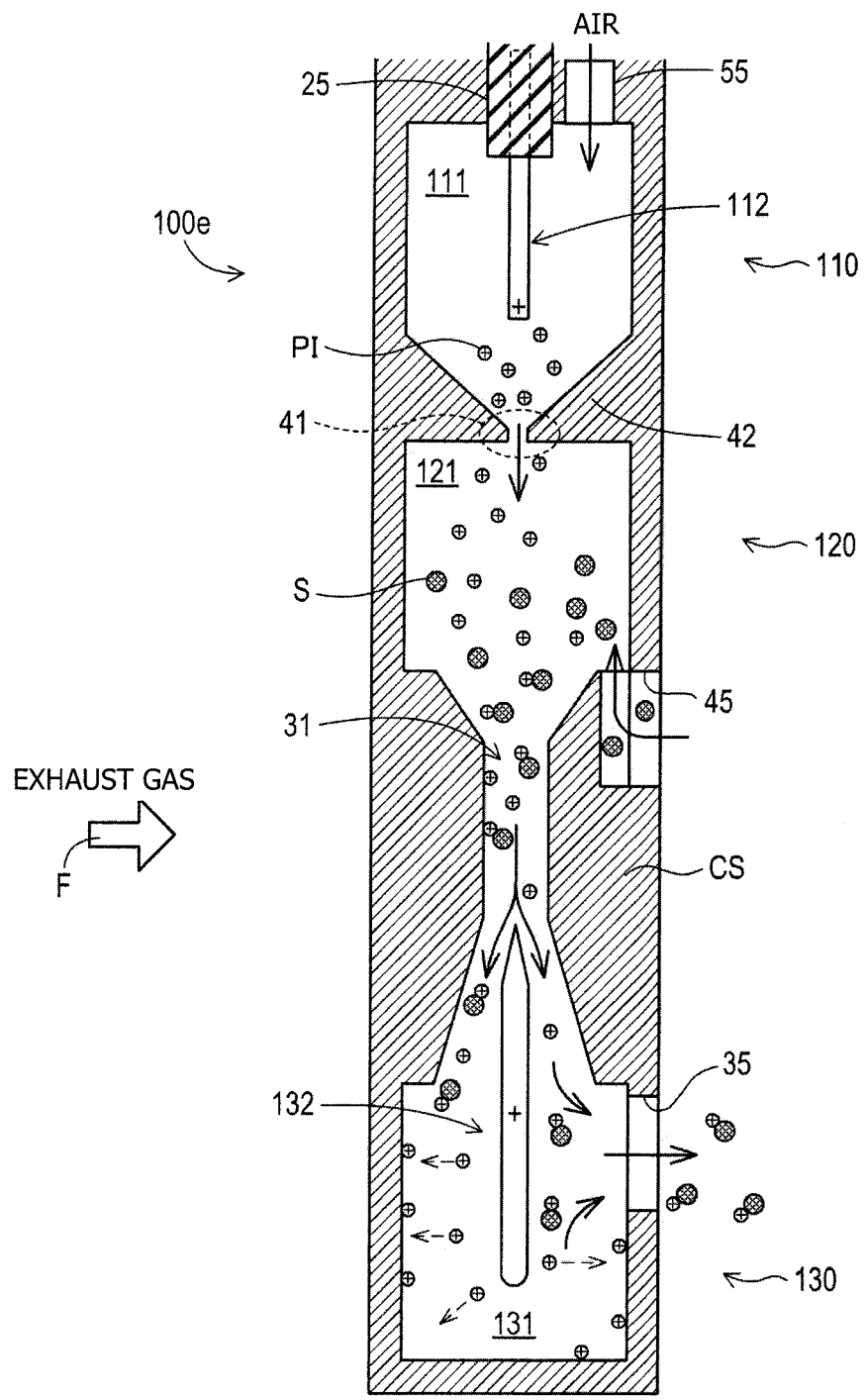
FIG. 2 is an explanatory view schematically showing a general structure of a distal end portion of a particulate sensor.

FIG. 2 is an explanatory view schematically showing the general structure of the distal end portion 100e of the particulate sensor 100.

The distal end portion 100e of the particulate sensor 100 includes an ion generation section 110, an exhaust gas electrification section 120, and an ion trapping section 130. The casing CS has a structure in which the three mechanism sections; i.e., the ion generation section 110, the exhaust gas electrification section 120, and the ion trapping section 130, are arranged in this order from the proximal end side (the upper side in FIG. 2) of the distal end portion 100e toward the distal end side (the lower side in FIG. 2) thereof (along the axial direction of the particulate sensor 100). The casing CS is formed of an electrically conductive material (for example, stainless steel or the like), and is connected to a secondary-side ground SGL (ground (ground line) whose potential serves as a reference potential for the secondary-side circuit in FIG. 3) through at least one of the corona cable 201 (specifically, a corona inner conductor 204 to be described later) and the auxiliary cable 211 (specifically, an auxiliary inner conductor 214 to be described later).

The ion generation section 110 is a mechanism section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1), and the high-pressure air supplied from the air supply section 800 (FIG. 1) is supplied to the ion generation chamber 111 through the air supply hole 55. The nozzle 41 is a very small hole (orifice) provided near the center of a partition wall 42 which separates the ion generation section 110 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a distal end portion of the first electrode 112 is located near the partition wall 42. The first electrode 112 is connected to the electric circuit section 700 (FIG. 1) through the corona cable 201 (specifically, a corona core wire 202 to be described later).

The ion generation section 110 is configured such that, by the electric power supplied from the electric circuit section 700, a voltage (e.g., 2 to 3 kV) is applied between the first electrode 112 (positive pole) and the partition wall 42 (negative pole). As a result of application of this voltage, the ion generation section 110 produces corona discharge between a distal end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1). The jetting speed of air jetted from the nozzle 41 may be set to a speed near the speed of sound.

The exhaust gas electrification section 120 is a section for electrifying the particulates contained in the exhaust gas by positive ions PI, and includes the electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI is jetted from the nozzle 41, a negative pressure is created in the electrification chamber 121, and the exhaust gas located outside the casing CS flows into the electrification chamber 121 through the inflow hole 45. Therefore, the air jetted from the nozzle 41 and containing the positive ions PI and the exhaust gas flowing inward through the inflow hole 45 are mixed together within the electrification chamber 121. At that time, at least a portion of the soot S (particulates) contained in the exhaust gas flowed inward through the inflow hole 45 is electrified by the positive ions PI supplied from the nozzle 41, whereby electrified particulates are produced. The air containing the electrified soot S (electrified particulates) and the positive ions PI not used for the electrification is supplied to the trapping chamber 131 of the ion trapping section 130 through the gas flow passage 31.

The ion trapping section 130 is a section for trapping ions not used for the electrification of the soot S (particulates), and includes the trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has the generally rod-like outer shape and is fixed to the casing CS such that its longitudinal direction coincides with the flow direction of air flowing through the gas flow passage 31 (the extending direction of the casing CS). The second electrode 132 is connected to the electric circuit section 700 (FIG. 1) through the auxiliary cable 211 (specifically, an auxiliary core wire 212 to be described later). The second electrode 132 is electrically insulated from the casing CS.

A voltage of about 100 V is applied to the second electrode 132, whereby it functions as an auxiliary electrode for assisting the trapping of positive ions not used for the electrification of the soot S. Specifically, by the electric power supplied from the electric circuit section 700, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for the electrification of soot S receive a repulsive force from the second electrode 132, whereby their advancing directions deviate to directions away from the second electrode 132. The positive ions PI whose advancing directions have been deviated are trapped by the inner circumferential walls of the trapping chamber 131 and the gas flow passage 31 which function as a negative pole. Meanwhile, the soot S (electrified particulates) to which positive ions PI have adhered also receives the repulsive force from the second electrode 132 as in the case of the positive ions PI themselves. However, since the soot S is larger in mass than the positive ions PI, the influence of the repulsive force on the advancing directions is smaller as compared with the case of the positive ions PI themselves. Therefore, the electrified soot S (electrified particulates) is discharged to the outside of the casing CS through the discharge hole 35 as a result of the flow of the exhaust gas.

Notably, a method of calculating the amount of soot S contained in the exhaust gas from the signal output from the particulate sensor 100 will be described later.

Figure 3:
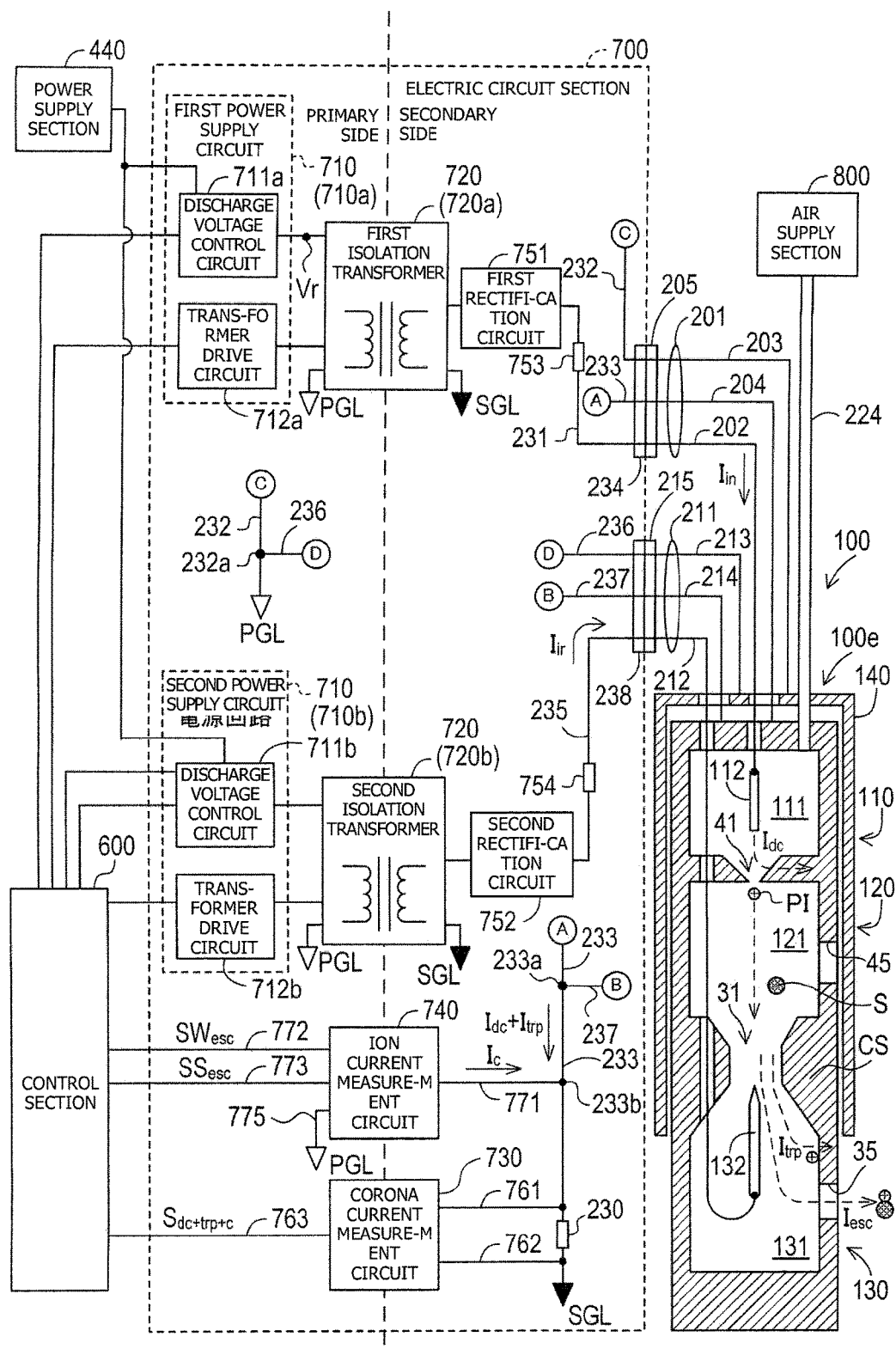
FIG. 3 is an explanatory view showing general electrical configurations of the particulate sensor and an electric circuit section.

FIG. 3 is an explanatory view sowing the electrical configurations of the particulate sensor 100 and the electric circuit section 700.

The particulate sensor 100 has a metallic support 140 which is formed of an electrically conductive material (for example, stainless steel or the like) and which supports the casing CS in a state in which the metallic support 140 is electrically insulated from the casing CS.

The metallic support 140 has a fixing portion (for example, a screw groove or the like) for fixation to the exhaust gas pipe 402 (see FIG. 1B). As a result of fixation to the exhaust gas pipe 402, the metallic support 140 is electrically connected to the exhaust gas pipe 402 and is connected to a primary-side ground PGL (ground (ground line) whose potential serves as a reference potential for the primary-side circuit).

The corona cable 201 is a so-called triaxial cable and includes the corona core wire 202, a corona outer conductor 203, a corona inner conductor 204, and a corona cable connector 205.

The corona core wire 202 is provided as a center conductor formed of an electrically conductive material (for example, copper or the like). The corona core wire 202 is electrically connected to the first electrode 112 of the particulate sensor 100. The corona inner conductor 204 is a tubular braided wire located on the radially outer side of the corona core wire 202 and electrically insulated from the corona core wire 202, and is formed by braiding thin wires of electrical conductive material (for example, copper or the like). The corona inner conductor 204 is electrically connected to the casing CS of the particulate sensor 100. The corona outer conductor 203 is a tubular braided wire located on the radially outer side of the corona inner conductor 204 and electrically insulated from the corona inner conductor 204, and is formed by braiding thin wires of electrical conductive material (for example, copper or the like). The corona outer conductor 203 is electrically connected to the metallic support 140 of the particulate sensor 100. The corona cable connector 205 is provided at the ends of the corona core wire 202, the corona outer conductor 203, and the corona inner conductor 204.

The auxiliary cable 211 is a so-called triaxial cable and includes an auxiliary core wire 212, an auxiliary outer conductor 213, an auxiliary inner conductor 214, and an auxiliary cable connector 215.

The auxiliary core wire 212 is provided as a center conductor formed of an electrically conductive material (for example, copper or the like). The auxiliary core wire 212 is electrically connected to the second electrode 132 of the particulate sensor 100. The auxiliary inner conductor 214 is a tubular braided wire located on the radially outer side of the auxiliary core wire 212 and electrically insulated from the auxiliary core wire 212, and is formed by braiding thin wires of electrical conductive material (for example, copper or the like). The auxiliary inner conductor 214 is electrically connected to the casing CS of the particulate sensor 100. The auxiliary outer conductor 213 is a tubular braided wire located on the radially outer side of the auxiliary inner conductor 214 and electrically insulated from the auxiliary inner conductor 214, and is formed by braiding thin wires of electrical conductive material (for example, copper or the like). The auxiliary outer conductor 213 is electrically connected to the metallic support 140 of the particulate sensor 100. The auxiliary cable connector 215 is provided at the ends of the auxiliary core wire 212, the auxiliary outer conductor 213, and the auxiliary inner conductor 214.

[1-3. Electric Circuit Section]

As shown in FIG. 3, the electric circuit section 700 includes a power supply circuit 710, an isolation transformer 720, a corona current measurement circuit 730, an ion current measurement circuit 740, a first rectification circuit 751, and a second rectification circuit 752.

Also, the electric circuit section 700 includes a corona current path 231, a first reference path 232, a first ion current path 233, a corona connector 234, an auxiliary current path 235, a second reference path 236, a second ion current path 237, and an auxiliary connector 238.

The corona current path 231 is a current path extending from the corona connector 234 to the first rectification circuit 751. A short protection resistor 753 is provided in the corona current path 231. The first reference path 232 is a current path extending from the corona connector 234 to the primary-side ground PGL. The first ion current path 233 is a current path extending from the corona connector 234 to the secondary-side ground SGL. The corona connector 234 is configured to be connectable with the corona cable connector 205.

When the corona cable connector 205 and the corona connector 234 are connected to each other, the corona core wire 202 is electrically connected to the corona current path 231, the corona outer conductor 203 is electrically connected to the first reference path 232, and the corona inner conductor 204 is electrically connected to the first ion current path 233.

The auxiliary current path 235 is a current path extending from the auxiliary connector 238 to the second rectification circuit 752, and auxiliary electrode current $I_{ir}$ flows through the current path. A short protection resistor 754 is provided in the auxiliary current path 235. The second reference path 236 is a current path extending from the auxiliary connector 238 to a connection point 232a of the first reference path 232 and is electrically connected to the primary-side ground PGL through the first reference path 232. The second ion current path 237 is a current path extending from the auxiliary connector 238 to a connection point 233a of the first ion current path 233 and is electrically connected to the secondary-side ground SGL through the first ion current path 233. The auxiliary connector 238 is configured to be connectable with the auxiliary cable connector 215.

When the auxiliary cable connector 215 and the auxiliary connector 238 are connected to each other, the auxiliary core wire 212 is electrically connected to the auxiliary current path 235, the auxiliary outer conductor 213 is electrically connected to the second reference path 236, and the auxiliary inner conductor 214 is electrically connected to the second ion current path 237.

The power supply circuit 710 includes a first power supply circuit 710a and a second power supply circuit 710b. The isolation transformer 720 includes a first isolation transformer 720a and a second isolation transformer 720b.

The first power supply circuit 710a supplies to the first isolation transformer 720a the electric power supplied from the power supply section 440, and drives the first isolation transformer 720a. The first power supply circuit 710a includes a first discharge voltage control circuit 711a and a first transformer drive circuit 712a. The first discharge voltage control circuit 711a is configured such that it can arbitrarily change the voltage value of the electric power supplied to the first isolation transformer 720a under the control by the control section 600. In the present embodiment, the control section 600 controls the voltage value of the electric power supplied to the first isolation transformer 720a such that the current value of input current $I_{in}$ supplied to the first electrode 112 of the particulate sensor 100 through the corona cable 201 (specifically, the corona core wire 202) becomes equal to a target current value $I_{ta}$ (e.g., 5 µA) set in advance. The method of this control by the control section 600 will be described later. As a result, the amount of positive ions PI generated by the corona discharge in the ion generation section 110 can be made constant.

The first transformer drive circuit 712a includes a switch which can switch the flow direction of current flowing through the primary coil of the first isolation transformer 720a. The first transformer drive circuit 712a drives the first isolation transformer 720a by the switching operation of the switch. In the present embodiment, the circuit type of the first isolation transformer 720a is a push-pull type. However, the circuit type of the first isolation transformer 720a is not limited thereto and may be, for example, a half-bridge type or a full-bridge type.

The first isolation transformer 720a performs voltage conversion for the electric power supplied from the first power supply circuit 710a, and supplies the voltage-converted electric power to the first rectification circuit 751 on the secondary side. The first isolation transformer 720a of the present embodiment is configured such that the primary coil and the secondary coil are not in physical contact with each other but are magnetically coupled with each other. A circuit on the primary side of the first isolation transformer 720a includes the control section 600 and the power supply section 440 as well as the first power supply circuit 710a. A circuit on the secondary side of the first isolation transformer 720a includes the particulate sensor 100 and the first rectification circuit 751.

The second power supply circuit 710b supplies to the second isolation transformer 720b the electric power supplied from the power supply section 440, and drives the second isolation transformer 720b. The second power supply circuit 710b includes a second discharge voltage control circuit 711b and a second transformer drive circuit 712b. The second discharge voltage control circuit 711b is configured such that it can arbitrarily change the voltage value of the electric power supplied to the second isolation transformer 720b under the control by the control section 600. In the present embodiment, the control section 600 controls the voltage value of the electric power supplied to the second isolation transformer 720b such that the voltage supplied to the second electrode 132 of the particulate sensor 100 through the auxiliary cable 211 (specifically, the auxiliary core wire 212) becomes equal to a target voltage value (e.g., 100 V) set in advance.

The second transformer drive circuit 712b includes a switch which can switch the flow direction of current flowing through the primary coil of the second isolation transformer 720b. The second transformer drive circuit 712b drives the second isolation transformer 720b by the switching operation of the switch. In the present embodiment, the circuit type of the second isolation transformer 720b is a push-pull type. However, the circuit type of the second isolation transformer 720b is not limited thereto and may be, for example, a half-bridge type or a full-bridge type.

The second isolation transformer 720b performs voltage conversion for the electric power supplied from the second power supply circuit 710b, and supplies the voltage-converted electric power to the second rectification circuit 752 on the secondary side. The second isolation transformer 720b of the present embodiment is configured such that the primary coil and the secondary coil are not in physical contact with each other but are magnetically coupled with each other. A circuit on the primary side of the second isolation transformer 720b includes the control section 600 and the power supply section 440 as well as the second power supply circuit 710b. A circuit on the secondary side of the second isolation transformer 720b includes the particulate sensor 100 and the second rectification circuit 752.

The corona current measurement circuit 730 and the ion current measurement circuit 740 are circuits provided between the circuit on the primary side of the isolation transformer 720 (the first isolation transformer 720a and the second isolation transformer 720b) and the circuit on the secondary side of the isolation transformer 720 (the first isolation transformer 720a and the second isolation transformer 720b), and are electrically connected to the primary-side and secondary-side circuits, respectively. As will be described later, the corona current measurement circuit 730 is configured such that a circuit portion electrically connected to the circuit on the primary side of the isolation transformer 720 (the first isolation transformer 720a and the second isolation transformer 720b) is physically insulated from a circuit portion electrically connected to the circuit on the secondary side of the isolation transformer 720 (the first isolation transformer 720a and the second isolation transformer 720b). Notably, as described above, the ground (ground line) which provides the reference potential of the primary-side circuit is also referred to as a "primary-side ground PGL," and the ground which provides the reference potential of the secondary-side circuit is also referred to as a "secondary-side ground SGL."

Ends of the primary coils of the isolation transformer 720 (the first isolation transformer 720a and the second isolation transformer 720b) are connected to the primary-side ground PGL, and ends of the secondary coils thereof are connected to the secondary-side ground SGL. First ends of the corona internal conductor 204 of the corona cable 201 and the auxiliary internal conductor 214 of the auxiliary cable 211 are connected to the casing CS, and second ends of the corona internal conductor 204 of the corona cable 201 and the auxiliary internal conductor 214 of the auxiliary cable 211 are connected to the secondary-side ground SGL through the first ion current path 233 and the second ion current path 237.

The first rectification circuit 751 is connected to the first electrode 112 through the short protection resistor 753, and supplies the converted electric power to the first electrode 112 through the corona core wire 202 of the corona cable 201. Namely, the voltage supplied from the first rectification circuit 751 becomes mostly a discharge voltage at the first electrode 112, and the current supplied from the first rectification circuit 751 becomes an input current $I_{in}$ input to the first electrode 112. The second rectification circuit 752 is connected to the second electrode 132 through the short protection resistor 754, and applies the converted voltage to the second electrode 132 through the auxiliary core wire 212 of the auxiliary cable 211.

The ion current measurement circuit 740 detects the current value of a current ($I_{esc}$) corresponding to the positive ions PI having flowed out without being trapped by the ion trapping section 130 and supplies to the secondary-side circuit a current (compensation current $I_c$) corresponding to the positive ions PI having flowed out. Namely, the ion current measurement circuit 740 supplies, as the compensation current $I_c$, to the secondary-side circuit, a current corresponding to the amount of the electrified soot S (electrified particulates) discharged from the particulate sensor 100 (the casing CS) to the outside. The ion current measurement circuit 740 is connected to the first ion current path 233 on the secondary side (specifically, a portion of the first ion current path 233 located between the connection point 223a and the shunt resistor 230) through a wiring line 771, and is connected to the control section 600 on the primary side through wiring lines 772 and 773. Also, the ion current measurement circuit 740 is connected to the primary-side ground PGL through the wiring line 775. Through the wiring line 772, the ion current measurement circuit 740 outputs to the control section 600 a signal $SW_{esc}$ showing a current value corresponding to the amount of positive ions PI having flowed out without being trapped by the ion trapping section 130. The ion current measurement circuit 740 also outputs a signal $SS_{esc}$ to the control section 600 through the wiring line 773, the signal $SS_{esc}$ being obtained by amplifying the signal $SW_{esc}$ and serving as a high sensitivity signal.

The corona current measurement circuit 730 is connected to the first ion current path 233 through wiring lines 761 and 762, and is connected to the control section 600 through a wiring line 763. The wiring lines 761 and 762 are connected to the first ion current path 233 such that the shunt resistor 230 provided in the first ion current path 233 is located between the wiring lines 761 and 762. The corona current measurement circuit 730 outputs to the control section 600 a signal $S_{dc+trp+c}$ representing the current value of a secondary-side current ($I_{dc}+I_{trp}+I_c$) flowing from the casing CS toward the secondary-side ground SGL through the first ion current path 233. Here, a "signal representing the current value" is not limited to a signal which directly represents the current value, and may be a signal which indirectly represents the current value. For example, the "signal representing the current value" may be a signal on the basis of which the current value can be specified by applying a computation expression or a map to information obtained from the signal. Notably, since the compensation current $I_c$ supplied (supplemented) from the ion current measurement circuit 740 corresponds to the current corresponding to the positive ions PI (electrified particulates) discharged from the particulate sensor 100 (the casing CS), the current value of the secondary-side current which includes the compensation current $I_c$ and which flows from the casing CS to the secondary-side ground SGL; i.e., the current value of the secondary-side current ($I_{dc}+I_{trp}+I_c$) flowing through the shunt resistor 230, becomes equal to the current value of the input current $I_{in}$.

Using the signal $S_{dc+trp+c}$ input from the corona current measurement circuit 730, the control section 600 controls the first discharge voltage control circuit 711a such that the current value of the input current $I_{in}$ becomes equal to the target current value $I_{ta}$. Namely, the corona current measurement circuit 730 and the control section 600 constitute a constant current circuit for maintaining the current value of the corona current (=the input current $I_{in}$) at a constant level. Since the current value of the corona current correlates with the amount of positive ions PI generated at the ion generation section 110, the amount of positive ions PI generated at the ion generation section 110 is maintained constant by this constant current circuit.

There will be described a method by which the ion current measurement circuit 740 detects the current value of the current corresponding to the positive ions PI having flowed out without being trapped by the ion trapping section 130.

Here, the current supplied from the corona core wire 202 of the corona cable 201 to the first electrode 112 is referred to as "input current $I_{in}$"; the current flowing from the first electrode 112 to the casing CS through the partition wall 42 due to corona discharge is referred to as "discharge current $I_{dc}$"; the current corresponding to the charge of the positive ions PI which are some of the positive ions PI generated due to corona discharge, are used for electrification of the soot S, and leak to the outside of the casing CS is referred to as "signal current $I_{esc}$"; and the current corresponding to the charge of the positive ions PI trapped by the casing CS is referred to as "trapped current $I_{trp}$." These four currents satisfy the relation of expression (1) shown in the following [F1].

[F1]

$$I_{in}=I_{dc}+I_{trp}+I_{esc} \tag{1}$$

Here, the signal current $I_{esc}$ is a signal which shows a current value corresponding to the current output from the ion current measurement circuit 740 (current (compensation current $I_c$)) corresponding to the positive ions PI having flowed out). Therefore, by detecting this compensation current $I_c$, the ion current measurement circuit 740 can detect the current value of the current ($I_{esc}$) corresponding to the positive ions PI having flowed out without being trapped by the ion trapping section 130.

Notably, the compensation current $I_c$ is also a signal representing the difference in potential between the primary-side ground PGL and the secondary-side ground SGL. Also, the compensation current $I_c$ is a current representing a current value equivalent to the signal current $I_{esc}$. In consideration of [F1], the compensation current $I_c$ has a current value corresponding to the difference between ($=I_{in}-I_{dc}-I_{trp}$) obtained by subtracting the current ($=I_{trp}$) corresponding to the amount of ions trapped by the ion trapping section 130 from the current ($=I_{in}-I_{dc}$) corresponding to the amount of ions generated at the ion generation section 110. Namely, the compensation current $I_c$ is a state quantity which correlates with the difference obtained by subtracting the amount of ions trapped by the ion trapping section 130 from the amount of ions generated at the ion generation section 110 by the ion electric power.

[1-4. Ion Current Measurement Circuit]

Figure 4:
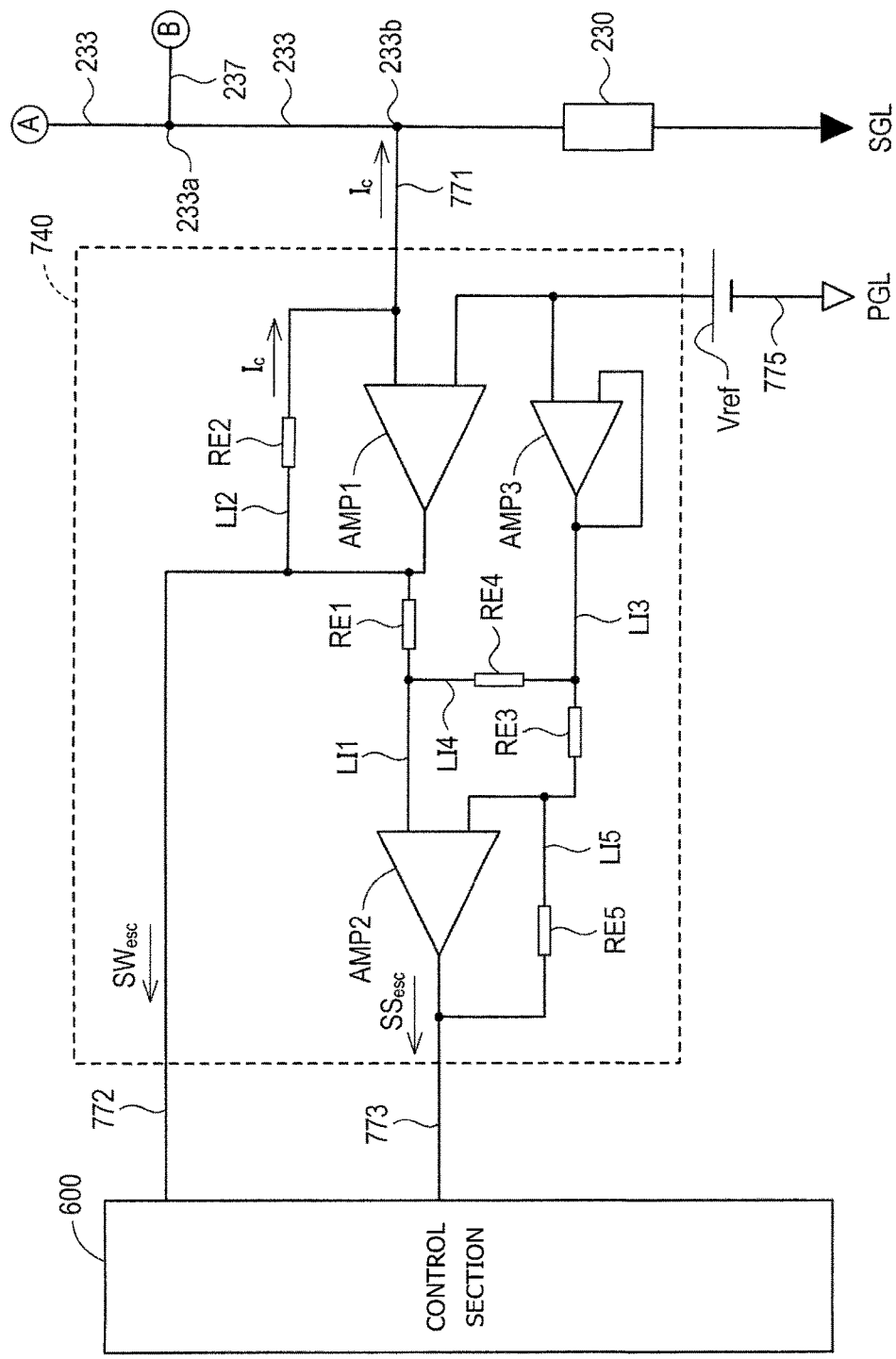
FIG. 4 is an explanatory view exemplifying a general configuration of an ion current measurement circuit.

FIG. 4 is an explanatory view exemplifying the general configuration of the ion current measurement circuit 740.

The ion current measurement circuit 740 includes a first operational amplifier AMP1, a second operational amplifier AMP2, a third operational amplifier AMPS, and resistors RE1 to RE5 having known resistances.

One input terminal of the first operational amplifier AMP1 is connected to the secondary-side ground SGL through the wiring line 771 and the first ion current path 233 (including the shunt resistor 230), and the other input terminal of the first operational amplifier AMP1 is connected to the primary-side ground PGL through the wiring line 775. The output terminal of the first operational amplifier AMP1 is connected to the control section 600 through the wiring line 772. Notably, a power source Vref for providing a constant reference voltage (for example, 0.5 V) in relation to the primary-side ground PGL is connected to the other input terminal of the first operational amplifier AMP1. By inputting the reference voltage to the first operational amplifier AMP1, it is possible to cause the potential difference between the two input terminals of the first operational amplifier AMP1 to approach a potential difference range within which an error (error due to bias current, offset voltage, etc.) is hardly produced. Also, the output terminal of the first operational amplifier AMP1 is connected to one input terminal of the second operational amplifier AMP2 through a portion of the wiring line 772 and a wiring line LI1, and is connected to the wiring line 771 through a portion of the wiring line 772 and a wiring line LI2. The resistor RE1 is provided in the wiring line LI1, and the resistor RE2 is provided in the wiring line LI2.

One input terminal of the second operational amplifier AMP2 is connected to the first operational amplifier AMP1 through a portion of the wiring line LI1 and the wiring line 772, and the other input terminal of the second operational amplifier AMP2 is connected to the primary-side ground PGL through a wiring line LI3 and the wiring line 775. The resistor RE3 and the third operational amplifier AMP3 are provided in the wiring line LI3. A wiring line LI4 is connected to a node between the resistor RE3 and the third operational amplifier AMP3. The wiring line LI3 is connected to the wiring line LI1 through the wiring line LI4 in which the resistor RE4 is provided. The third operational amplifier AMP3 is configured to function as a voltage follower which suppresses voltage change due to current change on the output side. The output terminal of the second operational amplifier AMP2 is connected to the control section 600 through the wiring line 773, and is connected to the wiring line LI3 through the wiring line 773 and a wiring line LI5. The resistor RE5 is provided in the wiring line LI5.

When a difference is produced between the reference potential of the secondary-side ground SGL and the reference potential of the primary-side ground PGL as a result of generation of the signal current $I_{esc}$, the first operational amplifier AMP1 outputs a voltage corresponding to this difference. Since the voltage output from the first operational amplifier AMP1 correlates with the current value of the signal current $I_{esc}$, this voltage value is output to the control section 600 through the wiring line 772 as a signal $SW_{esc}$ representing the current value of the signal current $I_{esc}$.

Also, the voltage output from the first operational amplifier AMP1 produces the compensation current $I_c$, which is supplied from the wiring line LI2 to the wiring line 771 through the resistor RE2. As described above, the current value of the compensation current $I_c$ is equal to the current value of the signal current $I_{esc}$. Therefore, as a result of supply of the compensation current $I_c$ to the wiring line 771 which constitutes the secondary-side circuit, the difference between the reference potential of the secondary-side ground SGL and the reference potential of the primary-side ground PGL is compensated.

The second operational amplifier AMP2 amplifies the signal $SW_{esc}$ input from the first operational amplifier AMP1, and outputs to the control section 600 the signal $SS_{esc}$ obtained as a result of the amplification. Since the second operational amplifier AMP2 is configured to function as a differential amplification circuit, the second operational amplifier AMP2 outputs a voltage corresponding to the difference between the voltage input to one input terminal as the signal $SW_{esc}$ and the reference potential of the primary-side ground PGL input to the other input terminal. Namely, the second operational amplifier AMP2 outputs a voltage to the control section 600 as the signal $SS_{esc}$, the voltage being obtained by amplifying the voltage of the input signal $SW_{esc}$ at a predetermined amplification factor (e.g., $10^3$ times).

The control section 600 detects the amount of soot S contained in the exhaust gas through use of the signal $SW_{esc}$ (low sensitivity signal) and the signal $SS_{esc}$ (high sensitivity signal) input from the ion current measurement circuit 740. No particular limitation is imposed on the method of detecting the amount of soot S contained in the exhaust gas by using these signals representing the current value of the signal current $I_{esc}$. For example, in the case where the control section 600 stores a map or a relational expression showing the relation between the voltage value of the signal and the amount of soot S contained in the exhaust gas, the control section 600 can calculate the amount of soot S contained in the exhaust gas by using the map or the relational expression.

The control section 600 of the present embodiment obtains each of the voltage values, which are analog signals input thereto as the signals $SS_{esc}$ and $SW_{esc}$, as a digital value of a predetermined resolution (for example, 8 bits). Also, the control section 600 is configured such that the size of the voltage readable range (the range of the full scale) becomes the same for the signals $SS_{esc}$ and $SW_{esc}$ input thereto.

The signal $SS_{esc}$ (high sensitivity signal) has a higher sensitivity (resolution) for the current value of the signal current $I_{esc}$ as compared with the signal $SW_{esc}$ (low sensitivity signal). For example, whereas a voltage level of the signal $SW_{esc}$ of 1 V corresponds to a magnitude of the signal current $I_{esc}$ of 1 nA, a voltage level of the signal $SS_{esc}$ of 1 V corresponds to a magnitude of the signal current $I_{esc}$ of 1 pA. Meanwhile, the control section 600 has the same voltage resolution (the minimum recognizable potential difference) (for example, 0.02 V) for both the signals $SS_{esc}$ and $SW_{esc}$. Accordingly, the current value of the signal current $I_{esc}$ corresponding to the voltage resolution of the control section 600 is small for the case of the signal $SS_{esc}$ (e.g., 0.02 pA) and is large for the case of the signal $SW_{esc}$ (e.g., 0.02 nA). In other words, the control section 600 can detect a smaller change in the signal current $I_{esc}$ from signal $SS_{esc}$, as compared with the signal $SW_{esc}$.

Therefore, the amount of soot S contained in the exhaust gas obtained from the signal $SS_{esc}$ is smaller in the minimum recognizable unit and is higher in accuracy than the amount of soot S contained in the exhaust gas obtained from the signal $SW_{esc}$. Meanwhile, the readable voltage range (e.g., 0 to 5 V) of the control section 600 is set to cover the entire voltage range of the signal $SW_{esc}$. Therefore, a range in which the amount of soot S contained in the exhaust gas can be measured through use of the signal $SW_{esc}$ is wider than a range in which the amount of soot S contained in the exhaust gas can be measured through use of the signal $SS_{esc}$. If the amount of soot S contained in the exhaust gas falls within a range corresponding to the entire voltage range of the signal $SW_{esc}$, the amount of soot S can be measured within the entire range.

As can be understood from the above, when the voltage value of the signal $SS_{esc}$ falls within the readable voltage range, the control section 600 can accurately measure the amount of soot S contained in the exhaust gas through use of the signal $SS_{esc}$, and when the voltage value of the signal $SS_{esc}$ falls outside the readable voltage range, the control section 600 can measure the amount of soot S contained in the exhaust gas through use of the signal $SW_{esc}$ which allows measurement within a wider range.

[1-5. Corona Current Measurement Circuit]

Figure 5:
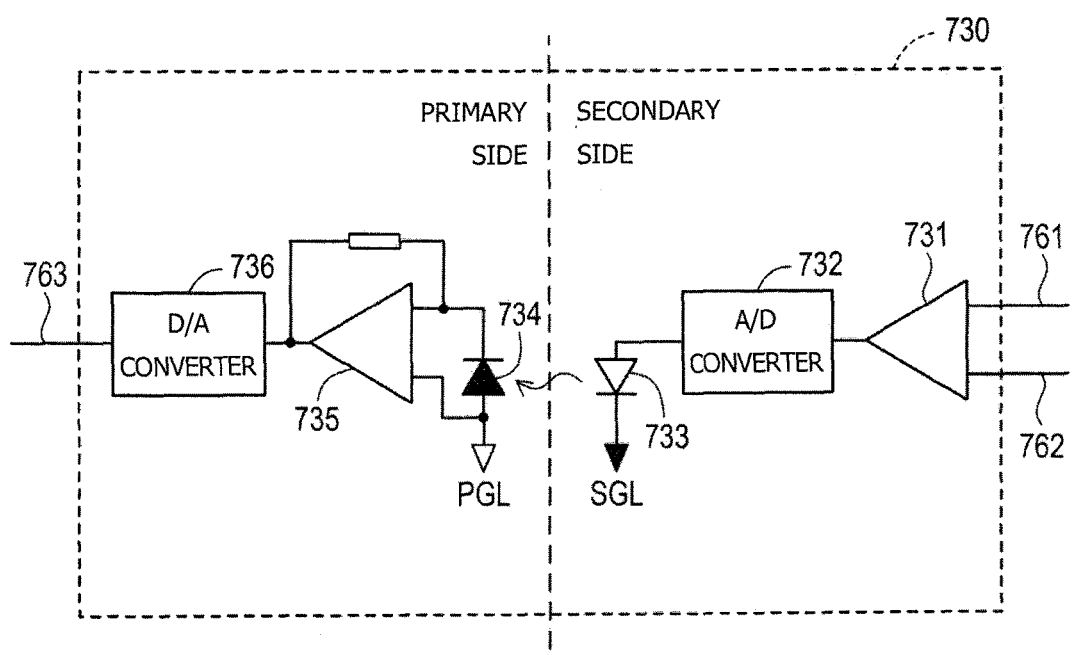
FIG. 5 is an explanatory view exemplifying a general configuration of a corona current measurement circuit.

FIG. 5 is an explanatory view exemplifying the general configuration of the corona current measurement circuit 730.

The corona current measurement circuit 730 is configured as a so-called optical-coupling-type isolation amplifier whose input and output sides are isolated from each other. The input side of the corona current measurement circuit 730 belongs to the secondary side of the electric circuit section 700 (FIG. 3), and the output side of the corona current measurement circuit 730 belongs to the primary side of the electric circuit section 700. The corona current measurement circuit 730 includes a secondary-side operational amplifier 731, an A/D converter 732, a light emitting section 733, a light receiving section 734, a primary-side operational amplifier 735, and a D/A converter 736.

The two input terminals of the secondary-side operational amplifier 731 are connected to the wiring line 761 and the wiring line 762, respectively, and the output terminal thereof is connected to the A/D converter 732. The secondary-side operational amplifier 731 amplifies the potential difference between the wiring line 761 and the wiring line 762 and outputs the amplified potential difference to the A/D converter 732. The potential difference between the wiring line 761 and the wiring line 762 is the potential difference between the opposite ends of the shunt resistor 230 (FIG. 3) whose resistance is known, and correlates with the current value of the current flowing through the first ion current path 233 (FIG. 3) (the secondary-side current $(I_{dc}+I_{trp}+I_c)$). Namely, the secondary-side operational amplifier 731 amplifies an analogue voltage signal representing the current value of the current flowing through the first ion current path 233 (FIG. 3) and outputs the amplified analogue voltage signal to the A/D converter 732.

The A/D converter 732, which is connected to the secondary-side operational amplifier 731 and the light emitting section 733, converts the analog signal output from the secondary-side operational amplifier 731 to a digital signal and outputs the digital signal to the light emitting section 733.

The light emitting section 733 includes an LED and is connected to the A/D converter 732 and the secondary-side ground SGL. The light emitting section 733 converts the digital voltage signal output from the A/D converter 732 to an optical signal.

The light receiving section 734 includes a photodiode and is connected to the primary-side operational amplifier 735 and the primary-side ground PGL. The light receiving section 734 converts the optical signal output from the light emitting section 733 to a current signal and outputs the current signal to the primary-side operational amplifier 735. In this manner, the light emitting section 733 and the light receiving section 734 are electrically and physically isolated from each other, and signals are transmitted between the light emitting section 733 and the light receiving section 734 through the mediation of light.

The primary-side operational amplifier 735 is connected to the light receiving section 734 and the D/A converter 736, and includes a current-voltage-conversion circuit. The primary-side operational amplifier 735 converts the current signal output from the light receiving section 734 to a voltage signal and outputs the voltage signal to the D/A converter 736. The D/A converter 736, which is connected to the primary-side operational amplifier 735 and the wiring line 763, converts the digital signal output from the primary-side operational amplifier 735 to an analog signal and outputs the analog signal to the control section 600 (FIG. 3) through the wiring line 763. Since the corona current measurement circuit 730 has the above-described configuration, the corona current measurement circuit 730 can output to the control section 600 on the primary side the signal input from the first ion current path 233 on the secondary side, while maintaining the isolation between the primary side and the secondary side.

[1-6. Processes Executed by Control Section]

The control section 600 includes a microcomputer and executes various types of processes. The control section 600 executes at least a particulate measurement process and an anomaly determination process as the various types of processes.

First, the particulate measurement process will be described briefly.

The particulate measurement process is a process for computing the amount of soot S by using the signals $SS_{esc}$ and $SW_{esc}$ from the ion current measurement circuit 740. For example, in the particulate measurement process, an ion current A corresponding to the signal current $I_{esc}$ is computed (measured) through use of the low sensitivity signal $SW_{esc}$ and the high sensitivity signal signals $SS_{esc}$ input from the ion current measurement circuit 740. Subsequently, in the particulate measurement process, the amount of soot S corresponding to the ion current A obtained through the measurement is computed through use of, for example, a map showing the relation between the ion current A and the amount of soot S in the exhaust gas or a relational expression representing the relation between the ion current A and the amount of soot S in the exhaust gas. Notably, the map, formulas, etc. may be stored in the storage section (RAM, etc.) of the control section 600 in advance.

After having computed the amount of soot S by the particulate measurement process, the control section 600 outputs to the informing section 920 a piece of information regarding the amount of soot S (the amount of particulates) obtained through the computation. As described above, the informing section 920 includes a display unit disposed on the casing 910, and displays the received piece of information on the display unit.

Figure 6:
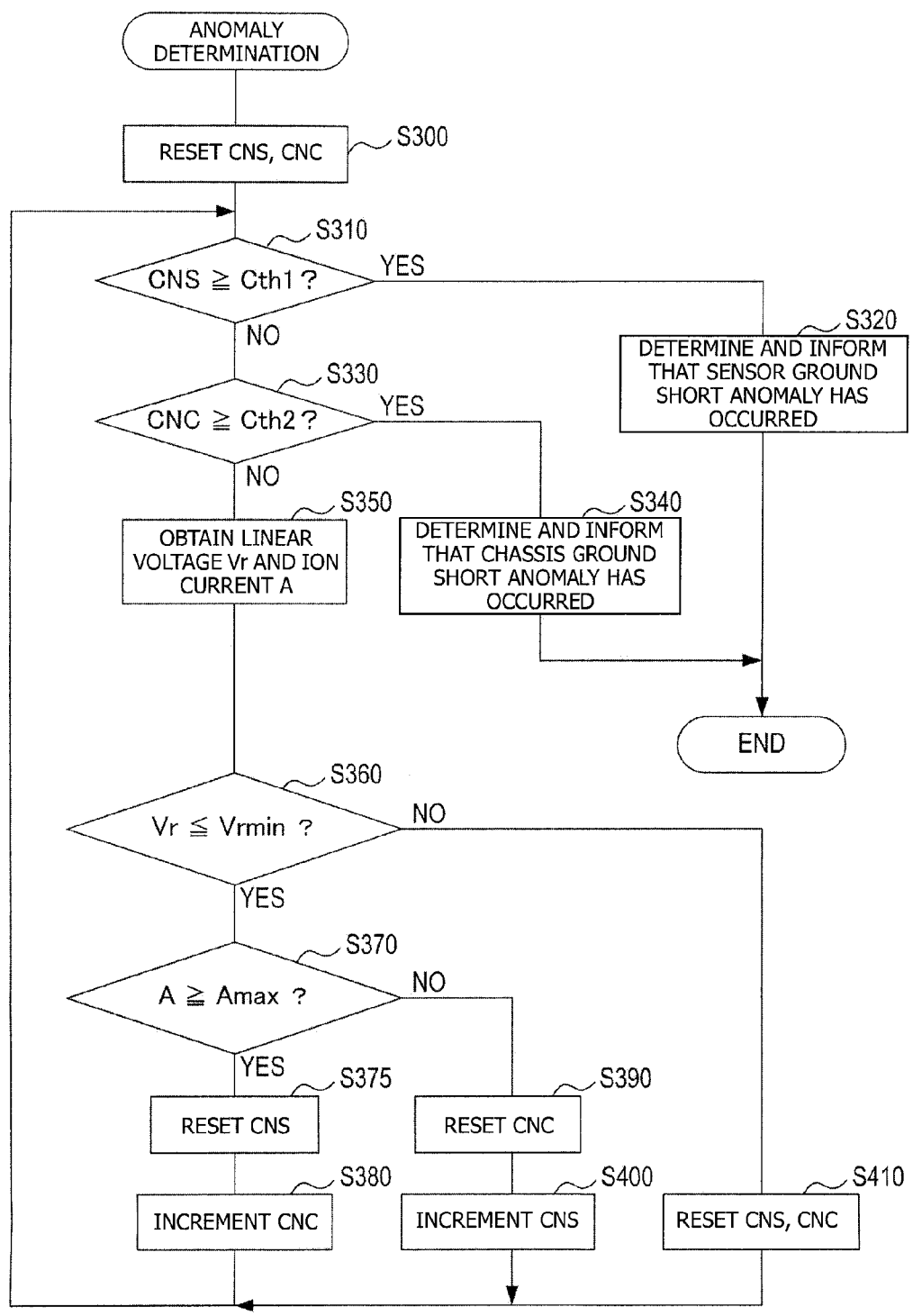
FIG. 6 is an flowchart representing the details of an anomaly determination process.

Next, the anomaly determination process will be described. FIG. 6 is a flowchart showing the details of the anomaly determination process. The anomaly determination process is a process for determining whether or not the corona core wire 202 is in a short anomaly state. The short anomaly state of the corona core wire 202 refers to a state in which the corona core wire 202 is electrically connected to the corona inner conductor 204 or the corona outer conductor 203. The anomaly determination process is executed when the control section 600 is started.

When the anomaly determination process is executed, first, in S300 (S stands for "step"), the control section 600 resets a sensor anomaly counter CNS and a chassis anomaly counter CNC (CNC=0, CNS=0).

The sensor anomaly counter CNS is a counter for counting the number of times of occurrence of a sensor-ground short anomaly (secondary-side ground short anomaly) of the corona core wire 202 in the particulate sensor 100. The sensor-ground short anomaly of the corona core wire 202 refers to an anomalous state in which the corona core wire 202 is electrically connected to the secondary-side ground SGL through the corona inner conductor 204, etc. Since the potential of the secondary-side ground SGL is the reference potential of the secondary-side circuit and is the reference potential for the first electrode 112 and the second electrode 132 of the particulate sensor 100, the secondary-side ground SGL is also referred to as the "sensor ground."

The chassis anomaly counter CNC is a counter for counting the number of times of occurrence of a chassis-ground short anomaly (primary-side ground short anomaly) of the corona core wire 202 in the particulate sensor 100. The chassis-ground short anomaly of the corona core wire 202 refers to an anomalous state in which the corona core wire 202 is electrically connected to the primary-side ground PGL through the corona outer conductor 203, etc. Since the potential of the primary-side ground PGL is the reference potential of the primary-side circuit and is the reference potential at the chassis (not shown) of the particulate measurement apparatus 300, the primary-side ground PGL is also referred to as the "chassis ground."

In S310 subsequent to S300, the control section 600 determines whether or not the number of times counted by the sensor anomaly counter CNS is equal to or greater than a predetermined sensor determination threshold Cth1 (for example, Cth1=1000 [times]). When the control section 600 makes an affirmative determination (Yes), the control section 600 proceeds to S320, and when the control section 600 makes a negative determination (No), the control section 600 proceeds to S330.

In the case where the control section 600 has proceeded to S320 as a result of the affirmative determination in S310, in S320, the control section 600 determines that the sensor-ground short anomaly (secondary-side ground short anomaly) of the corona core wire 202 has occurred in the particulate sensor 100 and executes a process of notifying (informing) that anomalous state. In S320, the control section 600 executes, as a notifying process (informing process), a process of displaying on the informing section 920 an anomaly informing image showing the sensor-ground short anomaly of the corona core wire 202.

In the case where the control section 600 has proceeded to S330 as a result of the negative determination in S310, in S330, the control section 600 determines whether or not the number of times counted by the chassis anomaly counter CNC is equal to or greater than a predetermined chassis determination threshold Cth2 (for example, Cth2=1000 [times]). When the control section 600 makes an affirmative determination (Yes), the control section 600 proceeds to S340, and when the control section 600 makes a negative determination (No), the control section 600 proceeds to S350.

In the case where the control section 600 has proceeded to S340 as a result of the affirmative determination in S330, in S340, the control section 600 determines that the chassis-ground short anomaly (primary-side ground short anomaly) of the corona core wire 202 has occurred in the particulate sensor 100 and executes a process of notifying (informing) that anomalous state. In S340, the control section 600 executes a process of displaying on the informing section 920 an anomaly informing image showing the chassis-ground short anomaly of the corona core wire 202.

In the case where the control section 600 has proceeded to S350 as a result of the negative determination in S330, in S350, the control section 600 obtains a linear voltage Vr and the ion current A. The linear voltage Vr is the voltage applied from the first discharge voltage control circuit 711a to the first isolation transformer 720a. The ion current A is the current computed in the particulate measurement process through use of the low sensitivity signal $SW_{esc}$ and the high sensitivity signal $SS_{esc}$; in other words, the ion current A is the signal current $I_{esc}$ (compensation current $I_c$) corresponding to the positive ions PI having flowed out without being trapped at the ion trapping section 130.

In S360 subsequent to S350, the control section 600 determines whether or not the linear voltage Vr is equal to or lower than a particular voltage value Vrmin (Vr≤Vrmin). When the control section 600 makes an affirmative determination (Yes), the control section 600 proceeds to S370, and when the control section 600 makes a negative determination (No), the control section 600 proceeds to S410.

In the case where the control section 600 has proceeded to S370 as a result of the affirmative determination in S360, in S370, the control section 600 determines whether or not the ion current A is equal to or larger than a first current value Amax (A≥Amax). When the control section 600 makes an affirmative determination (Yes), the control section 600 proceeds to S375, and when the control section 600 makes a negative determination (No), the control section 600 proceeds to S390.

Notably, when the chassis-ground short anomaly of the corona core wire 202 (the anomalous state in which the corona core wire 202 is electrically connected to the corona outer conductor 203) has occurred, the electric power (specifically, current) supplied from the first isolation transformer 720a (specifically, its secondary coil) is supplied to the primary-side ground PGL through the corona outer conductor 203, and the supply of electric power to the first electrode 112 becomes impossible.

When the chassis-ground short anomaly of the corona core wire 202 has occurred as described above, there is created a state which is the same as the state in which substantially all the ions have been discharged to the outside of the particulate sensor 100 (the casing CS). Therefore, the ion current measurement circuit 740 supplies the compensation current $I_c$ having a large magnitude to the first ion current path 233 such that the current value of the secondary-side current $(I_{dc}+I_{trp}+I_c)$ flowing through the shunt resistor 230 becomes substantially equal to the current value of the input current $I_{in}$ (target current value $I_{ta}$). The current value of the compensation current $I_c$ at that time falls within a region which is a portion of the numerical range within which the signal current $I_{esc}$ falls when the corona core wire 202 is normal, the region being equal to or greater than the first current value Amax.

Also, when the chassis-ground short anomaly of the corona core wire 202 has occurred, the corona current measurement circuit 730 outputs to the control section 600 a signal representing a current value which is substantially equal to the target current value $I_{ta}$ as the signal $S_{dc+trp+c}$. The control section 600 having received such a signal $S_{dc+trp+c}$ determines that the input current $I_{in}$ has substantially reached the target current value $I_{ta}$ and controls the linear voltage Vr output from the first discharge voltage control circuit 711a to become equal to or lower than the particular voltage value Vrmin.

As can be understood from the above, when the chassis-ground short anomaly of the corona core wire 202 has occurred, the linear voltage Vr becomes equal to or lower than the particular voltage value Vrmin, and the ion current A becomes equal to or larger than the first current value Amax. Therefore, in S360 and S370, the control section 600 determines, on the basis of the values of the linear voltage Vr and the ion current A, whether or not the chassis-ground short anomaly of the corona core wire 202 has occurred. Namely, in the case where the control section 600 makes an affirmative determination in S360 and an affirmative determination in S370, the control section 600 can determine that the chassis-ground short anomaly of the corona core wire 202 has occurred.

In the case where the control section 600 has proceeded to S375 as a result of the affirmative determination in S370, in S375, the control section 600 resets the sensor anomaly counter CNS (CNS=0). In S380 subsequent to S375, the control section 600 increments (adds 1 to) the chassis anomaly counter CNC.

In the case where the control section 600 has proceeded to S390 as a result of the negative determination in S370, in S390, the control section 600 resets the chassis anomaly counter CNC (CNC=0).

Notably, when the sensor-ground short anomaly of the corona core wire 202 (the anomalous state in which the corona core wire 202 is electrically connected to the corona inner conductor 204) has occurred, the electric power (in other words, current) supplied from the first isolation transformer 720a (specifically, its secondary coil) is supplied to the secondary-side ground SGL through the corona inner conductor 204, and the supply of electric power to the first electrode 112 becomes impossible. In this case, since the amount of positive ions PI generated at the first electrode 112 by means of corona discharge becomes 0, both the trapped current $I_{trp}$ and the discharge current $I_{dc}$ flowing from the first electrode 112 to the casing CS through corona discharge become substantially 0.

However, when the sensor-ground short anomaly of the corona core wire 202 has occurred, the input current $I_{in}$ supplied from the first isolation transformer 720a (the first rectification circuit 751) flows to the secondary-side ground SGL through the corona core wire 202, the corona inner conductor 204, and the first ion current path 233. Therefore, the current value of "$I_{dc}+I_{trp}$" which flows through the first ion current path 233 becomes substantially equal to the current value of the input current $I_{in}$. Namely, the input current $I_{in}$ supplied from the first isolation transformer 720a (the first rectification circuit 751) flows to the secondary-side ground SGL through the first ion current path 233 and the shunt resistor 230 without passing through the first electrode 112 and the casing CS.

Even in such a situation, the ion current measurement circuit 740 supplies the compensation current $I_c$ to the first ion current path 233 such that the current value of the secondary-side current $(I_{dem}+I_{trp}+I_c)$ flowing through the shunt resistor 230 becomes equal to the current value of the input current $I_{in}$ (the target current value $I_{ta}$). Namely, since the current value of "$I_{dc}+I_{trp}$" which flows through the first ion current path 233 is substantially equal to the current value of the input current $I_{in}$ (the target current value $I_{ta}$), the ion current measurement circuit 740 tries to decrease the compensation current $I_c$ supplied to the first ion current path 233. Notably, the current value of the compensation current $I_c$ at that time becomes smaller than the first current value Amax.

Also, when the sensor-ground short anomaly of the corona core wire 202 has occurred, the input current $I_{in}$ (having a current value equal to the target current value $I_{ta}$) supplied from the first isolation transformer 720a (the first rectification circuit 751) flows through the shunt resistor 230. Therefore, the corona current measurement circuit 730 outputs to the control section 600 a signal representing a current value which is substantially equal to the target current value $I_{ta}$ as the signal $S_{dc+trp+c}$. The control section 600 having received such a signal $S_{dc+trp+c}$ determines that the input current $I_{in}$ has substantially reached the target current value $I_{ta}$ and controls the linear voltage Vr output from the first discharge voltage control circuit 711a to become equal to or lower than the particular voltage value Vrmin.

As can be understood from the above, when the sensor-ground short anomaly of the corona core wire 202 has occurred, the linear voltage Vr becomes equal to or lower than the particular voltage value Vrmin, and the ion current A becomes smaller than the first current value Amax. Therefore, in S360 and S370, the control section 600 determines, on the basis of the values of the linear voltage Vr and the ion current A, whether or not the sensor-ground short anomaly of the corona core wire 202 has occurred. Namely, in the case where the control section 600 makes an affirmative determination in S360 and a negative determination in S370, the control section 600 can determine that the sensor-ground short anomaly of the corona core wire 202 has occurred.

When the control section 600 has proceeded to S400 after completion of S390, in S400, the control section 600 increments (adds 1 to) the sensor anomaly counter CNS.

In the case where the control section 600 has proceeded to S410 as a result of the negative determination is S360, in S410, the control section 600 resets the sensor anomaly counter CNS and the chassis anomaly counter CNC (CNS=0, CNC=0).

After the execution of any of S380, S400, and S410, the control section 600 again proceeds to S310. The control section 600 repeatedly executes the anomaly determination process until it makes an affirmative determination in S310 or S330.

Notably, in the anomaly determination process, the period between a point in time when S310 is executed one time and a point in time when S310 is executed again (in other word, the execution interval of S310) is set to 10 msec, and in S310, the control section 600 determines whether or not the sensor-ground short anomaly of the corona core wire 202 has continued for 10 sec (=10 msec×Cth1 (=1000 times)) or longer. Also, in the anomaly determination process, the period between a point in time when S330 is executed one time and a point in time when S330 is executed again (in other word, the execution interval of S330) is set to 10 msec, and in S330, the control section 600 determines whether or not the chassis-ground short anomaly of the corona core wire 202 has continued for 10 sec (=10 msec×Cth2 (=1000 times)) or longer.

Namely, in the anomaly determination process, when the control section 600 determines that the sensor-ground short anomaly of the corona core wire 202 has continued for 10 sec or longer (an affirmative determination in S310), the control section 600 determines that the sensor-ground short anomaly has occurred and executes a process for notifying (informing) that anomalous state (S320). Also, in the anomaly determination process, when the control section 600 determines that the chassis-ground short anomaly of the corona core wire 202 has continued for 10 sec or longer (an affirmative determination in S330), the control section 600 determines that the chassis-ground short has occurred and executes a process for notifying (informing) that anomalous state (S340).

[1-7. Effects]

As described above, the particulate measurement apparatus 300 in the particulate measurement system 10 of the present embodiment is configured such that the anomaly determination process is executed in the control section 600.

In the particulate measurement apparatus 300, when an anomaly of the electrical connection state has occurred at the corona cable 201 (specifically, the corona core wire 202), the ion generation section 110 (specifically, the first electrode 112), etc., the supply of electric power from the first isolation transformer 720a (specifically, its secondary coil) to the ion generation section 110 (the first electrode 112) is not performed properly. Notably, examples of the anomaly of the electrical connection state include an anomaly of short between the corona core wire 202 and the corona inner conductor 204 and an anomaly of short between the corona core wire 202 and the corona outer conductor 203.

In this case, since the ion generation section 110 cannot generate ions properly, the generation of electrified particulates at the electrification chamber 121 cannot be performed properly, and the trapping of ions at the ion trapping section 130 cannot be performed properly. Therefore, the current flowing from the ion trapping section 130 to the first ion current path 233 through the corona inner conductor 204 exhibits an anomalous behavior different from that in the case where the electrical connection state is normal. As a result, the secondary-side current which flows between the secondary-side ground SGL and the point 233b on the first ion current path 233 to which the compensation current $I_c$ is supplied (in other word, the secondary-side current ($I_{dc}$+$I_{trp}$+$I_c$) flowing through the shunt resistor 230) also exhibits an anomalous behavior different from that in the case where the electrical connection state is normal.

Notably, the corona current measurement circuit 730 and the control section 600 control the amount of electric power supplied to the first isolation transformer 720a (specifically, its primary coil) on the basis of the secondary-side current ($I_{dc}$+$I_{trp}$+$I_c$). Therefore, in the case where the secondary-side current ($I_{dc}$+$I_{trp}$+$I_c$) exhibits an anomalous behavior, the state of control of the amount of electric power supplied to the first isolation transformer 720a (specifically, its primary coil) by the corona current measurement circuit 730 and the control section 600 becomes a special state different from that in the case where the secondary-side current ($I_{dc}$+$I_{trp}$+$I_c$) is normal.

Therefore, the control section 600 which executes the anomaly determination process can determine the anomaly of the electrical connection state at the corona cable 201 (specifically, the corona core wire 202), the ion generation section 110 (specifically, the first electrode 112), etc. on the state of control of the amount of electric power supplied to the first isolation transformer 720a (specifically, its primary coil) on the basis of the secondary-side current ($I_{dc}$+$I_{trp}$+$I_C$).

Therefore, in the particulate measurement apparatus 300, the anomaly of the electrical connection state at the corona cable 201 (specifically, the corona core wire 202), the ion generation section 110 (specifically, the first electrode 112), etc. can be determined without directly directing the voltage at the corona cable 201 (specifically, the corona core wire 202) or the ion generation section 110 (specifically, the first electrode 112).

The control section 600 determines whether or not the linear voltage Vr is equal to or lower than the particular voltage value Vrmin in the anomaly determination process (S360). When the linear voltage Vr is equal to or lower than the particular voltage value Vrmin, the control section 600 provisionally determines that the corona core wire 202 is in a short anomaly state and increments the sensor anomaly counter CNS or the chassis anomaly counter CNC (S380, S400).

When the count value of the sensor anomaly counter CNS is equal to or greater than the sensor determination threshold Cth1 (affirmative determination in S310) or when the count value of the chassis anomaly counter CNC is equal to or greater than the chassis determination threshold Cth2 (affirmative determination in S330), the control section 600 determines that the corona core wire 202 is in the short anomaly state (S320, S340).

Namely, the control section 600 does not immediately determine that the corona core wire 202 is in the short anomaly state when the linear voltage Vr becomes equal to or lower than the particular voltage value Vrmin. Instead, the control section 600 determines that the corona core wire 202 is in the short anomaly state when the state in which the linear voltage Vr is equal to or lower than the particular voltage value Vrmin continues for a short anomaly time (10 sec in the present embodiment) or longer (S320, S340). The short anomaly time is determined in advance on the basis of the execution intervals of S310 and the sensor determination threshold Cth1 and is determined in advance on the basis of the execution intervals of S330 and the chassis determination threshold Cth2.

By performing the anomaly determination in the above-described manner, the control section 600 does not erroneously determine that the corona core wire 202 is in the short anomaly state in the case where the linear voltage Vr temporarily becomes equal to or lower than the particular voltage value Vrmin due to the influence of noise or the like.

Therefore, in the particulate measurement apparatus 300, since the frequency of occurrence of erroneous determination due to the influence of noise or like can be decreased, the determination accuracy in determining the short anomaly state of the corona core wire 202 can be improved.

The control section 600 is configured to determine whether the short anomaly of the corona core wire 202 is the sensor-ground short anomaly (the secondary-side ground short anomaly) or the chassis-ground short anomaly (the primary-side ground short anomaly) by performing the determination on the basis of not only the state of the linear voltage Vr (S360) but also the state of the ion current A (S370).

As described above, in the particulate measurement apparatus 300, when the anomaly of the electrical connection state has occurred at the corona cable 201 (the corona core wire 202), the ion generation section 110 (the first electrode 112), etc., the supply of electric power from the first isolation transformer 720a (specifically, its secondary coil) to the ion generation section 110 (the first electrode 112) is not performed properly. In this case, since the ion generation section 110 cannot generate ions properly, the generation of electrified particulates at the electrification chamber 121 cannot be performed properly, and the trapping of ions at the ion trapping section 130 cannot be performed properly. Therefore, the compensation current $I_c$ which correlates with the difference obtained by subtracting the amount of ions trapped at the ion trapping section 130 from the amount of ions generated at the ion generation section 110 exhibits an anomalous behavior different from that in the case where the electrical connection state is normal.

Like the compensation current $I_c$ (the signal current $I_{esc}$), the ion current A is a state quantity which correlates with the difference obtained by subtracting the amount of ions trapped at the ion trapping section 130 from the amount of ions generated at the ion generation section 110.

Because of this, the control section 600 can determine whether the short anomaly of the corona core wire 202 is the sensor-ground short anomaly (the secondary-side ground short anomaly) or the chassis-ground short anomaly (the primary-side ground short anomaly) by performing the determination on the basis of the state of the ion current A (S370) in addition to the state of the linear voltage Vr (S360).

Therefore, the particulate measurement apparatus 300 can improve the determination accuracy through use of a plurality of determination factors, including at least the linear voltage Vr and the ion current A, as compared with the case where the determination is made through use of a single determination factor.

The control section 600 determines that the corona core wire 202 is in the short anomaly state (S320, S340) when the count value of the sensor anomaly counter CNS is equal to or greater than the sensor determination threshold Cth1 (affirmative determination in S310) or when the count value of the chassis anomaly counter CNC is equal to or greater than the chassis determination threshold Cth2 (affirmative determination in S330).

Namely, the control section 600 does not immediately determine that the corona core wire 202 is in the short anomaly state on the basis of the results of the determinations in S360 and S370. Instead, the control section 600 determines that the corona core wire 202 is in the short anomaly state when the state in which the corona core wire 202 is determined to be in the short anomaly state on the basis of the results of the determinations in S360 and S370 continues for the short anomaly time (10 sec in the present embodiment) or longer (S320, S340).

By performing the anomaly determination in the above-described manner, the control section 600 does not erroneously determine that the corona core wire 202 is in the short anomaly state in the case where the corona core wire 202 is temporarily determined to be in the short anomaly state on the basis of the results of the determinations in S360 and S370 due to the influence of noise or the like. Further, the control section 600 can determine whether the short anomaly state of the corona core wire 202 is the chassis-ground short anomaly state or the sensor-ground short anomaly state.

Therefore, since the particulate measurement apparatus 300 can determine the type of the short anomaly state of the corona core wire 202 (the chassis-ground short anomaly state, the sensor-ground short anomaly state) and can decrease the frequency of occurrence of erroneous determination due to the influence of noise or the like, the particulate measurement apparatus 300 can improve the determination accuracy in determining the short anomaly state of the corona core wire 202.

When the control section 600 makes an affirmative determination in S310 of the anomaly determination process, the control section 600 determines that the sensor-ground short anomaly (the secondary-side ground short anomaly) of the corona core wire 202 has occurred and executes a process of notifying (informing) that anomalous state (S320). Also, when the control section 600 makes an affirmative determination in S330 of the anomaly determination process, the control section 600 determines that the chassis-ground short anomaly (the primary-side ground short anomaly) of the corona core wire 202 has occurred and executes a process of notifying (informing) that anomalous state (S340). As the notifying process (informing process), the control section 600 executes a process of displaying on the informing section 920 an anomaly informing image showing the short anomaly (the sensor-ground short anomaly, the chassis-ground short anomaly) of the corona core wire 202.

The particulate measurement apparatus 300 including such a control section 600 can inform a user of the particulate measurement apparatus 300 of the short anomaly state of the corona core wire 202 through the informing section 920, to thereby prompt the user of the particulate measurement apparatus 300 to check the connection state of the corona cable 201 or to exchange the corona cable 201.

As a result, the particulate measurement apparatus 300 can prevent the particulate measurement using the particulate sensor 100 from being continued in a situation in which the corona core wire 202 is in the short anomaly state, to thereby prevent lowering of the measurement performance of the particulate sensor 100.

The particulate measurement system 10, which is configured by connecting the particulate sensor 100 to the above-described particulate measurement apparatus 300 through the corona cable 201, can determine the anomaly of the electrical connection state at the corona cable 201 (the corona core wire 202), the ion generation section 110 (the first electrode 112), etc. without directly detecting the voltage at the corona cable 201 (specifically, the corona core wire 202) or the ion generation section 110 (specifically, the first electrode 112).

[1-8. Correspondence of Wording]

Here, the correspondence of wording will be described.

The particulate measurement system 10 corresponds to an example of the particulate measurement system; the particulate measurement apparatus 300 corresponds to an example of the particulate measurement apparatus; the particulate sensor 100 corresponds to an example of the particulate sensor; the corona cable 201 corresponds to an example of the corona cable; and the informing section 920 corresponds to an example of the informing section.

The first isolation transformer 720a corresponds to an example of the isolation transformer for corona discharge; the first ion current path 233 and the second ion current path 237 correspond to an example of the signal line; the primary-side ground PGL corresponds to an example of the primary-side potential; the secondary-side ground SGL corresponds to an example of the secondary-side potential; the control section 600 and the ion current measurement circuit 740 correspond to an example of the particulate computation section; the control section 600 and the corona current measurement circuit 730 correspond to an example of the corona discharge control section; and the control section 600 executing the anomaly determination process corresponds to an example of the anomaly determination section. The current range equal to or greater than the first current value Amax corresponds to an example of the current increase anomaly range.

The ion generation section 110 corresponds to an example of the ion generation section; the electrification chamber 121 corresponds to an example of the electrification chamber; the ion trapping section 130 corresponds to an example of the trapping section; and the metallic support 140 corresponds to an example of the metallic support. The corona core wire 202 corresponds to an example of the corona core wire; the corona inner conductor 204 corresponds to an example of the inner shield wire; and the corona outer conductor 203 corresponds to an example of the outer shield wire.

2. Other Embodiment

An embodiment of the present invention has been described; however, the present invention is not limited to the above-described embodiment and can be implemented in various forms without departing from the gist of the invention.

For example, the anomaly determination process of the above-described embodiment is configured to determine whether or not the corona core wire 202 is in the short anomaly state on the basis of the linear voltage Vr and the ion current A. However, the anomaly determination process may be configured to determine whether or not the corona core wire 202 is in the short anomaly state on the basis of the linear voltage Vr only. Through employment of such a configuration, the determination process can be simplified, and the computation process load in the control section 600 can be reduced.

The determination procedure in S370 of the anomaly determination process is not limited to the above-described procedure. For example, the determination procedure may be such that the control section 600 determines whether or not "the ion current A is equal to or smaller than a second current value Amin (A≤Amin); when the control section 600 makes a negative determination, the control section 600 proceeds to S375; and when the control section 600 makes an affirmative determination, the control section 600 proceeds to S390." Even in S370 of such a determination procedure, the control section 600 can determine whether the short anomaly state of the corona core wire 202 is the chassis-ground short anomaly state or the sensor-ground short anomaly state. In this case, the current range greater than the second current value Amin corresponds to an example of the current increase anomaly range.

Alternatively, the determination procedure in S370 of the anomaly determination process may be such that "when the ion current A is equal to or greater than the first current value Amax (A≥Amax), the the control section 600 makes an affirmative determination and proceeds to S375; and when the ion current A is equal to or smaller than the second current value Amin (A≤Amin), the the control section 600 makes a negative determination and proceeds to S390." Even in S370 of such a determination procedure, the control section 600 can determine whether the short anomaly state of the corona core wire 202 is the chassis-ground short anomaly state or the sensor-ground short anomaly state. In this case, a current range equal to or greater than the first current value Amax may be defined as a current increase anomaly range, and a current range equal to or less than the second current value Amin may be defined as a current drop anomaly range.

The numerical value of the sensor determination threshold Cth1 and the numerical value of the chassis determination threshold Cth2 are not limited to the above-described numerical values, and proper values may be set in accordance with application or environment of use. In other words, the determination value for the continuation time of the anomalous state in S310 and S330 is not limited to 10 sec (=10 msec×Cth1 (=1000 times)), and may be set to 5 sec, 20 sec, etc. in accordance with application or environment of use.

The informing section 920 is not limited to the display unit, and may be a sound output unit which outputs an anomaly informing sound informing the short anomaly of the corona core wire. Alternatively, the informing section may include both the display unit and the sound output unit.

Also, in the above-described embodiment, the particulate sensor 100 has the second electrode 132. However, the particulate sensor may be configured without use of the second electrode 132. Even when the second electrode 132 is omitted, the amount of particulates can be measured on the basis of the amount of electrified particulates, and the structure of the particulate sensor can be made simpler to a degree corresponding to the omission of the second electrode 132. In such a case, the second power supply circuit 710b, the second isolation transformer 720b, the second rectification circuit 752, the short protection resistor 754, and the auxiliary current path 235 may be omitted from the electric circuit section 700.

Also, the structure of the particulate sensor which constitutes the particulate measurement system is not limited to the structure in which the ion generation section is disposed in line outside the exhaust gas electrification section. For example, there can be employed a structure in which the ion generation section is disposed inside the exhaust gas electrification section. Further, in the case where the particulate sensor constituting the particulate measurement system is configured such that the ion generation section is disposed inside the exhaust gas electrification section, the air supply section may be omitted from the particulate measurement apparatus, and the particulate sensor may have a structure in which the supply of high-pressure air to the electrification chamber by the air supply section is not performed. For example, such a particulate sensor may have a sensor structure disclosed in Japanese Patent Application Laid-Open (kokai) No. 2015-129711 of a patent application filed by the applicant of the present application, and the entirety of the disclosure is incorporated herein by reference.

Also, the corona current measurement circuit is not limited to the optical-coupling-type isolation amplifier and may be, for example, a magnetic-coupling-type or capacitive-coupling-type isolation amplifier.

Further, the corona cable is not limited to the triaxial cable (a cable in which the corona core wire, the corona inner conductor, and the corona outer conductor are coaxially disposed in this order from the inner side toward the outer side). For example, a cable in which the corona core wire, the corona inner conductor, the corona outer conductor are disposed in parallel, and the corona inner conductor and the corona outer conductor do not cover the corona core wire may be used as the corona cable. Alternatively, a cable which is composed of a first cable including the corona core wire and the corona inner conductor and a second cable including the corona outer conductor and in which the first cable and the second cable can be separated from each other may be used as the corona cable.

DESCRIPTION OF SYMBOLS

10: particulate measurement system, 100: particulate sensor, 110: ion generation section, 111: ion generation chamber, 112: first electrode, 120: exhaust gas electrification section, 121: electrification chamber, 130: ion trapping section, 132: second electrode, 140: metallic support, 201: corona cable, 202: corona core wire, 203: corona outer conductor, 204: corona inner conductor, 205: corona cable connector, 211: auxiliary cable, 212: auxiliary core wire, 213: auxiliary outer conductor, 214: auxiliary inner conductor, 215: auxiliary cable connector, 233: first ion current path, 235: auxiliary current path, 236: second reference path, 237: second ion current path, 300: particulate measurement apparatus, 600: control section, 700: electric circuit section, 710: power supply circuit, 710a: first power supply circuit, 710b: second power supply circuit, 711a: first discharge voltage control circuit, 711b: second discharge voltage control circuit, 712a: first transformer drive circuit, 712b: second transformer drive circuit, 720: isolation transformer, 720a: first isolation transformer, 720b: second isolation transformer, 730: corona current measurement circuit, 740: ion current measurement circuit, 751: first rectification circuit, 752: second rectification circuit, 800: air supply section, 920: informing section, 930: operation input section, CS: casing, PGL: primary-side ground, SGL: secondary-side ground.

The invention claimed is:

1. A particulate measurement apparatus which is adapted to be electrically connected to a particulate sensor for detecting particulates contained in a target gas and which controls the particulate sensor so as to measure the amount of the particulates contained in the target gas, said particulate sensor including: an ion generation section for generating ions by corona discharge; an electrification chamber into which the target gas is introduced and which electrifies, by using the ions, the particulates contained in the target gas to thereby produce electrified particulates; an ion trapping section which traps the ions generated by the ion generation section but which are not used for the electrification of the particulates; and a metal support which supports the ion generation section, the electrification chamber, and the trapping section in a condition in which the metal support is electrically insulated from the ion generation section, the electrification chamber, and the trapping section, the particulate measurement apparatus comprising:

an isolation transformer for corona discharge which has a primary coil and a secondary coil, and which performs voltage conversion;
a signal line which forms at least a portion of a signal path extending from the trapping section to a line of a secondary-side reference potential which is a reference potential of the secondary coil;
a particulate computation section which computes the amount of the particulates contained in the target gas on the basis of a current value of compensation current supplied to the signal line in accordance with the amount of the electrified particulates discharged from the particulate sensor; and
a corona discharge control section which controls the amount of electric power supplied to the primary coil, on the basis of secondary-side current flowing through the signal path, so as to control ion electric power generated at the secondary coil, wherein
the particulate measurement apparatus is electrically connected to the particulate sensor through a corona cable which includes a corona core wire, an inner shield wire, and an outer shield wire,
the corona core wire forms at least a portion of a path for supplying electric power from the secondary coil to the ion generation section,
the inner shield wire is electrically connected to the trapping section and the signal line in a state in which the inner shield wire is electrically insulated from the corona core wire,
the outer shield wire is electrically connected to the metal support and a line of a primary-side reference potential which is a reference potential of the primary coil in a state in which the outer shield wire is electrically insulated from the corona core wire and the inner shield wire, and
the particulate measurement apparatus further comprises an anomaly determination section which determines whether or not the corona core wire is in a short anomaly state on the basis of a state of control of the amount of electric power supplied to the primary coil by the corona discharge control section, the short anomaly state being an anomalous state in which the corona core wire is electrically connected to the inner shield wire or the outer shield wire.

2. The particulate measurement apparatus according to claim 1, wherein the anomaly determination section determines that the corona core wire is in the short anomaly state when the state of control of the amount of electric power supplied to the primary coil by the corona discharge control section is a voltage drop anomalous control state in which a voltage applied to the primary coil falls within a predetermined voltage drop anomaly range.

3. The particulate measurement apparatus according to claim 2, wherein the anomaly determination section determines that the corona core wire is in the short anomaly state when the voltage drop anomalous control state created by the corona discharge control section continues for a predetermined short anomaly time or longer.

4. The particulate measurement apparatus according to claim 1, wherein
the anomaly determination section determines whether the short anomaly state is a primary-side short anomaly or a secondary-side short anomaly on the basis of the current value of the compensation current in addition to the state of control of the amount of electric power supplied to the primary coil by the corona discharge control section, the primary-side short anomaly is an anomalous state in which the corona core wire is electrically connected to the outer shield wire, and the secondary-side short anomaly is an anomalous state in which the corona core wire is electrically connected to the inner shield wire.

5. The particulate measurement apparatus according to claim 4, wherein the anomaly determination section determines that the short anomaly state is the primary-side short anomaly, in which the corona core wire is electrically connected to the outer shield wire, in the case where the current value of the compensation current falls within a predetermined current increase anomaly range and the state of control of the amount of electric power supplied to the primary coil by the corona discharge control section is a voltage drop anomalous control state in which a voltage applied to the primary coil falls within a predetermined voltage drop anomaly range, and the anomaly determination section determines that the short anomaly state is the secondary-side short anomaly, in which the corona core wire is electrically connected to the inner shield wire, in the case where the current value of the compensation current does not fall within the current increase anomaly range and the state of control of the amount of electric power supplied to the primary coil by the corona discharge control section is the voltage drop anomalous control state.

6. The particulate measurement apparatus according to claim 5, wherein the anomaly determination section determines that the short anomaly state is the primary-side short anomaly, in which the corona core wire is electrically connected to the line of the primary-side reference potential, in the case where a state in which the state of control of the amount of electric power supplied to the primary coil by the corona discharge control section is the voltage drop anomalous control state and the current value of the compensation current falls within the current increase anomaly range continues for a predetermined primary short anomaly time or longer, and the anomaly determination section determines that the short anomaly state is the secondary-side short anomaly, in which the corona core wire is electrically connected to the line of the secondary-side reference potential, in the case where a state in which the state of control of the amount of electric power supplied to the primary coil by the corona discharge control section is the voltage drop anomalous control state and the current value of the compensation current does not fall within the current increase anomaly range continues for a predetermined secondary short anomaly time or longer.

7. The particulate measurement apparatus according to claim 1, further comprising an informing section which informs that the corona core wire is in the short anomaly state in the case where the anomaly determination section determines that the corona core wire is in the short anomaly state.

8. A particulate measurement system comprising:
a particulate sensor for detecting particulates contained in a target gas; and
the particulate measurement apparatus according to claim 1 which is adapted to be electrically connected to the particulate sensor through a corona cable and which controls the particulate sensor so as to measure the amount of the particulates contained in the target gas.

* * * * *